US010322060B2

(12) United States Patent
Fleischacker et al.

(10) Patent No.: US 10,322,060 B2
(45) Date of Patent: Jun. 18, 2019

(54) MOBILE DEVICE CONTROL

(71) Applicant: ZOLL Medical Corporation, Chelmsford, MA (US)

(72) Inventors: Justin Tyler Fleischacker, Bedford, NH (US); Guy R. Johnson, Gloucester, MA (US); Gary A. Freeman, Waltham, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 0 days.

(21) Appl. No.: 15/070,619

(22) Filed: Mar. 15, 2016

(65) Prior Publication Data

US 2016/0193109 A1 Jul. 7, 2016

Related U.S. Application Data

(62) Division of application No. 14/036,503, filed on Sep. 25, 2013.

(51) Int. Cl.
*A61H 31/00* (2006.01)
*A61N 1/39* (2006.01)
(Continued)

(52) U.S. Cl.
CPC ......... *A61H 31/005* (2013.01); *A61B 5/0408* (2013.01); *A61N 1/3925* (2013.01);
(Continued)

(58) Field of Classification Search
CPC .. A61N 1/36128; A61N 1/37247; A61N 1/39; A61N 1/3993; A61N 1/3925;
(Continued)

(56) References Cited

U.S. PATENT DOCUMENTS 3,513,850 A 5/1970 Weber
3,865,101 A 2/1975 Saper et al.
(Continued)

FOREIGN PATENT DOCUMENTS

GB 2314618 1/1998
GB 2314648 1/1998
(Continued)

OTHER PUBLICATIONS

Aase et al., "Compression Depth Estimation for CPR Quality Assessment Using DSP on Accelerometer Signals," IEEE Transactions on Biomedical Engineering, vol. 49, No. 3, Mar. 2002.
(Continued)

*Primary Examiner* — Steven O Douglas
(74) *Attorney, Agent, or Firm* — ZOLL Medical Corporation

(57) ABSTRACT

A system includes a processor coupled to a memory, the processor and memory configured to determine a proficiency level of a user of a rescue application based on stored data indicative of the user's proficiency level, and based on the user's proficiency level, select a level of operation for the rescue application. The rescue application is executed on a mobile device and configured to control operation of an AED. Each of multiple levels of operation for the rescue application allows the user a different degree of control over the operation of the AED. The processor and memory are configured to present, to the user, a set of instructions associated with the selected level of operation; and to enable control of the AED according to the selected levels of operation. A different set of instructions is associated with each of the multiple levels.

45 Claims, 29 Drawing Sheets

(51) Int. Cl.
*A61B 5/0408* (2006.01)
*G09B 23/28* (2006.01)

(52) U.S. Cl.
CPC ......... *A61N 1/3987* (2013.01); *A61N 1/3993* (2013.01); *G09B 23/288* (2013.01); *A61H 2201/5084* (2013.01)

(58) Field of Classification Search
CPC .. A61N 1/3987; G08B 21/02; G08B 21/0453; G06F 19/3418; A61H 31/005; A61H 2201/5084; G09B 23/288
See application file for complete search history.

(56) References Cited

U.S. PATENT DOCUMENTS

| | | |
|---|---|---|
| 4,019,501 A | 4/1977 | Harris |
| 4,077,400 A | 3/1978 | Harrigan |
| 4,088,138 A | 5/1978 | Diack et al. |
| 4,095,590 A | 6/1978 | Harrigan |
| 4,193,064 A | 3/1980 | Snyder |
| 4,198,963 A | 4/1980 | Barkalow et al. |
| 4,198,964 A | 4/1980 | Honneffer |
| RE30,372 E | 8/1980 | Mirowski et al. |
| 4,273,114 A | 6/1981 | Barkalow et al. |
| 4,326,507 A | 4/1982 | Barkalow |
| 4,491,423 A | 1/1985 | Cohen |
| 4,588,383 A | 5/1986 | Parker et al. |
| 4,610,254 A | 9/1986 | Morgan et al. |
| 4,619,265 A | 10/1986 | Morgan et al. |
| 4,757,821 A | 7/1988 | Snyder |
| 4,797,104 A | 1/1989 | Laerdal et al. |
| 4,863,385 A | 9/1989 | Pierce |
| 4,928,674 A | 5/1990 | Halperin et al. |
| 4,932,879 A | 6/1990 | Ingenito et al. |
| 5,081,993 A | 1/1992 | Kitney et al. |
| 5,193,537 A | 3/1993 | Freeman |
| 5,241,302 A | 8/1993 | Thong |
| 5,247,945 A | 9/1993 | Heinze et al. |
| 5,285,792 A | 2/1994 | Sjoquist et al. |
| 5,330,526 A | 7/1994 | Fincke et al. |
| 5,342,404 A | 8/1994 | Alt et al. |
| 5,348,008 A | 9/1994 | Bornn et al. |
| RE34,800 E | 11/1994 | Hutchins |
| 5,391,187 A | 2/1995 | Freeman |
| 5,409,010 A | 4/1995 | Beach et al. |
| 5,431,685 A | 7/1995 | Alt |
| 5,454,779 A | 10/1995 | Lurie et al. |
| 5,466,244 A | 11/1995 | Morgan |
| 5,472,453 A | 12/1995 | Alt et al. |
| 5,474,574 A | 12/1995 | Payne et al. |
| 5,496,257 A | 3/1996 | Kelly |
| 5,507,778 A | 4/1996 | Freeman |
| 5,511,553 A | 4/1996 | Segalowitz |
| 5,514,079 A | 5/1996 | Dillon |
| 5,533,958 A | 7/1996 | Wilk |
| 5,534,851 A | 7/1996 | Russek |
| 5,562,710 A | 10/1996 | Olsen et al. |
| 5,591,213 A | 1/1997 | Morgan |
| 5,611,815 A | 3/1997 | Cole et al. |
| 5,617,853 A | 4/1997 | Morgan |
| 5,619,265 A | 4/1997 | Suzuki et al. |
| 5,645,522 A | 7/1997 | Lurie et al. |
| 5,645,571 A | 7/1997 | Olson et al. |
| 5,662,690 A | 9/1997 | Cole et al. |
| 5,700,281 A | 12/1997 | Brewer et al. |
| 5,735,879 A | 4/1998 | Gliner et al. |
| 5,787,880 A | 8/1998 | Swanson et al. |
| 5,792,190 A | 8/1998 | Olson et al. |
| 5,853,292 A | 12/1998 | Eggert et al. |
| 5,913,685 A | 6/1999 | Hutchins |
| 5,993,398 A | 11/1999 | Alperin |
| 6,021,349 A | 2/2000 | Arand et al. |
| 6,120,442 A | 9/2000 | Hickey |
| 6,125,299 A | 9/2000 | Groenke et al. |
| 6,155,257 A | 12/2000 | Lurie et al. |
| 6,178,357 B1 | 1/2001 | Gliner et al. |
| 6,185,458 B1 | 2/2001 | Ochs et al. |
| 6,193,519 B1 | 2/2001 | Eggert et al. |
| 6,220,866 B1 | 4/2001 | Amend et al. |
| 6,224,562 B1 | 5/2001 | Lurie et al. |
| 6,238,349 B1 | 5/2001 | Hickey |
| 6,306,107 B1 | 10/2001 | Myklebust et al. |
| 6,334,070 B1 | 12/2001 | Nova et al. |
| 6,351,671 B1 | 2/2002 | Myklebust et al. |
| 6,356,785 B1 | 3/2002 | Snyder et al. |
| 6,371,765 B1 | 4/2002 | Wall et al. |
| 6,390,996 B1 | 5/2002 | Halperin et al. |
| 6,428,323 B1 | 8/2002 | Pugh |
| 6,443,735 B1 | 9/2002 | Eggert et al. |
| 6,503,087 B1 | 1/2003 | Eggert et al. |
| 6,572,547 B2 | 6/2003 | Miller et al. |
| 6,575,914 B2 | 6/2003 | Rock et al. |
| 6,752,771 B2 | 6/2004 | Rothman et al. |
| 6,827,695 B2 | 12/2004 | Palazzolo et al. |
| 6,961,612 B2 | 11/2005 | Elghazzawai et al. |
| 7,010,344 B2 | 3/2006 | Burnes et al. |
| 7,072,712 B2 | 7/2006 | Kroll et al. |
| 7,108,665 B2 | 9/2006 | Halperin |
| 7,118,542 B2 | 10/2006 | Palazzolo et al. |
| 7,122,007 B2 | 10/2006 | Querfuth et al. |
| 7,122,014 B2 | 10/2006 | Palazzolo |
| 7,164,945 B2 | 1/2007 | Hamilton et al. |
| 7,190,999 B2 | 3/2007 | Geheb et al. |
| 7,220,235 B2 | 5/2007 | Geheb et al. |
| 7,310,553 B2 | 12/2007 | Freeman |
| 7,429,250 B2 | 9/2008 | Halperin |
| 7,454,244 B2 | 11/2008 | Kassab et al. |
| 7,761,139 B2 | 7/2010 | Tearney et al. |
| 7,822,470 B2 | 10/2010 | Osypka et al. |
| 7,837,669 B2 | 11/2010 | Dann et al. |
| 7,846,138 B2 | 12/2010 | Dann et al. |
| 7,993,290 B2 | 8/2011 | Lund |
| 8,012,135 B2 | 9/2011 | Dann et al. |
| 8,034,006 B2 | 10/2011 | Celik-Butler |
| 8,096,962 B2 | 1/2012 | Palazzolo |
| 8,121,681 B2 | 2/2012 | Hampton |
| 8,147,433 B2 | 4/2012 | Halperin |
| 8,333,720 B2 | 12/2012 | Nysaether |
| 8,428,664 B1 | 4/2013 | Wyers |
| 2001/0011159 A1 | 8/2001 | Cantrell et al. |
| 2001/0018562 A1 | 8/2001 | Sherman et al. |
| 2002/0024888 A1 | 2/2002 | Schreiber |
| 2002/0026131 A1 | 2/2002 | Halperin |
| 2002/0026229 A1 | 2/2002 | Weil et al. |
| 2002/0055694 A1 | 5/2002 | Halperin et al. |
| 2002/0165471 A1 | 11/2002 | Halperin et al. |
| 2002/0193711 A1 | 12/2002 | Halperin et al. |
| 2003/0014055 A1 | 1/2003 | Svadovskiy |
| 2003/0032988 A1 | 2/2003 | Fincke et al. |
| 2003/0055460 A1 | 3/2003 | Owen et al. |
| 2003/0083699 A1 | 5/2003 | Hamilton et al. |
| 2003/0192547 A1 | 10/2003 | Lurie et al. |
| 2004/0039313 A1 | 2/2004 | Shermen et al. |
| 2004/0039419 A1 | 2/2004 | Stickney et al. |
| 2004/0049118 A1 | 3/2004 | Ideker et al. |
| 2004/0058305 A1 | 3/2004 | Lurie et al. |
| 2004/0044374 A1 | 4/2004 | Weinberg et al. |
| 2004/0162510 A1 | 8/2004 | Jayne et al. |
| 2004/0162585 A1 | 8/2004 | Elghazzawi et al. |
| 2004/0162586 A1 | 8/2004 | Covey et al. |
| 2004/0162587 A1 | 8/2004 | Hampton et al. |
| 2004/0186525 A1 | 9/2004 | Burnes et al. |
| 2004/0210171 A1 | 10/2004 | Palazzolo et al. |
| 2004/0214148 A1 | 10/2004 | Salvino et al. |
| 2004/0230140 A1 | 11/2004 | Steen |
| 2004/0267324 A1 | 12/2004 | Geheb |
| 2004/0267325 A1 | 12/2004 | Geheb et al. |
| 2005/0119706 A1 | 6/2005 | Ideker et al. |
| 2005/0209503 A1 | 9/2005 | Elliott |
| 2005/0214148 A1 | 9/2005 | Ogawa et al. |
| 2005/0256415 A1 | 11/2005 | Tan et al. |
| 2006/0009809 A1 | 1/2006 | Marcovecchio et al. |
| 2006/0036292 A1 | 2/2006 | Smith et al. |

(56) References Cited

U.S. PATENT DOCUMENTS

| | | |
|---|---|---|
| 2006/0041278 A1 | 2/2006 | Cohen et al. |
| 2006/0089574 A1 | 4/2006 | Paradis |
| 2006/0116724 A1 | 6/2006 | Snyder |
| 2006/0224053 A1 | 10/2006 | Black et al. |
| 2006/0257377 A1 | 11/2006 | Atala et al. |
| 2006/0270952 A1 | 11/2006 | Freeman et al. |
| 2007/0219588 A1 | 9/2007 | Freeman |
| 2008/0171311 A1 | 7/2008 | Centen |
| 2008/0176199 A1 | 7/2008 | Stickney et al. |
| 2010/0022904 A1 | 1/2010 | Centen |
| 2010/0049266 A1 | 2/2010 | Ochs |
| 2011/0009164 A1 | 1/2011 | Amiri |
| 2011/0117878 A1 | 5/2011 | Barash |
| 2012/0010543 A1 | 1/2012 | Johnson |
| 2012/0112903 A1 | 5/2012 | Kaib et al. |
| 2012/0136286 A1 | 5/2012 | Nova |
| 2012/0184882 A1 | 7/2012 | Totman |
| 2012/0226204 A1 | 9/2012 | Coleman |
| 2013/0030326 A1 | 1/2013 | Bogdanowicz |
| 2013/0045037 A1* | 2/2013 | Schaffer ............... G06F 1/163 400/472 |
| 2013/0111342 A1* | 5/2013 | Alameh ............... G06F 3/0488 715/702 |
| 2013/0282069 A1 | 10/2013 | Thiagarajan |
| 2014/0043149 A1 | 2/2014 | Cowan et al. |
| 2015/0109125 A1 | 4/2015 | Kaib et al. |

FOREIGN PATENT DOCUMENTS

| | | |
|---|---|---|
| WO | 1996/010984 | 4/1996 |
| WO | 1998/030282 | 7/1998 |
| WO | 1999/024114 | 5/1999 |
| WO | 1999/025306 | 5/1999 |
| WO | 1999/063926 | 12/1999 |
| WO | 1999/065560 | 12/1999 |
| WO | 2001/056652 | 8/2001 |
| WO | 2001/066182 | 9/2001 |
| WO | 2002/015836 | 2/2002 |
| WO | 2002/072197 | 9/2002 |
| WO | 2003/009895 | 2/2003 |
| WO | 2004/037154 | 5/2004 |
| WO | 2004/054656 | 7/2004 |
| WO | 2004/073493 | 9/2004 |
| WO | 2004/078259 | 9/2004 |
| WO | 2005/021089 | 3/2005 |

OTHER PUBLICATIONS

Abella et al., Chest Compression Rates During Cardiopulmonary Resuscitation Are Suboptimal, Circulation, 2005; 111:428-434.

American Red Cross—Adult CPR/AED Training—Workplace Programs, http://www.redcross.org/hss/cpraed.html, printed from Internet May 14, 1999.

Babbs, Charles F., Efficacy of interposed abdominal compression-cardiopulmonary resuscitation (CPR), active compression and decompression-CPR, and Lifestick CPR: Basic physiology in a spreadsheet model, Crit. Care Med. 2000 vol. 28, No. 11 (Suppl.).

Eftestol et al., Circulation, 2000, Predicting Outcome of Defibrillation by Spectral Characterization and Nonparametric Classification of Ventricular Fibrillation in Patients With Out-of-Hospital Cardiac Arrest.

Flewelling, Nellcor Incorporated, Noninvasive Optical Monitoring, Chap. 88, pp. 1346-1353. CRC Press, Inc., 1995.

Force Sensing Resistors—An Overview of the Technology, FSR Integration Guide & Evaluation Parts Catalog with Suggested Electrical Interfaces (no date).

Gruben et al., "System for Mechanical Measurements During Cardiopulmonary Resuscitation in Humans," IEEE Transactions on Biomedical Engineering, vol. 37, No. 2, Feb. 1990.

Heartstream—The Background Behind Our Technology, http://www.heartstream.com/techbk.htm, printed from Internet Jun. 25, 1999.

Pinsky, M.R., et al., Hemodynamic effects of cardiac cycle-specific increases in intrathoracic pressure, Journal of Applied Physiology, vol. 60(2), pp. 604-612, Feb. 1986.

Sato et al., Critical Care Medicine, vol. 25(5), May 1997, pp. 733-736.

Yu et al., Circulation, 2002, Adverse Outcomes of Interrupted Precordial Compression During Automated Defibrillation.

* cited by examiner

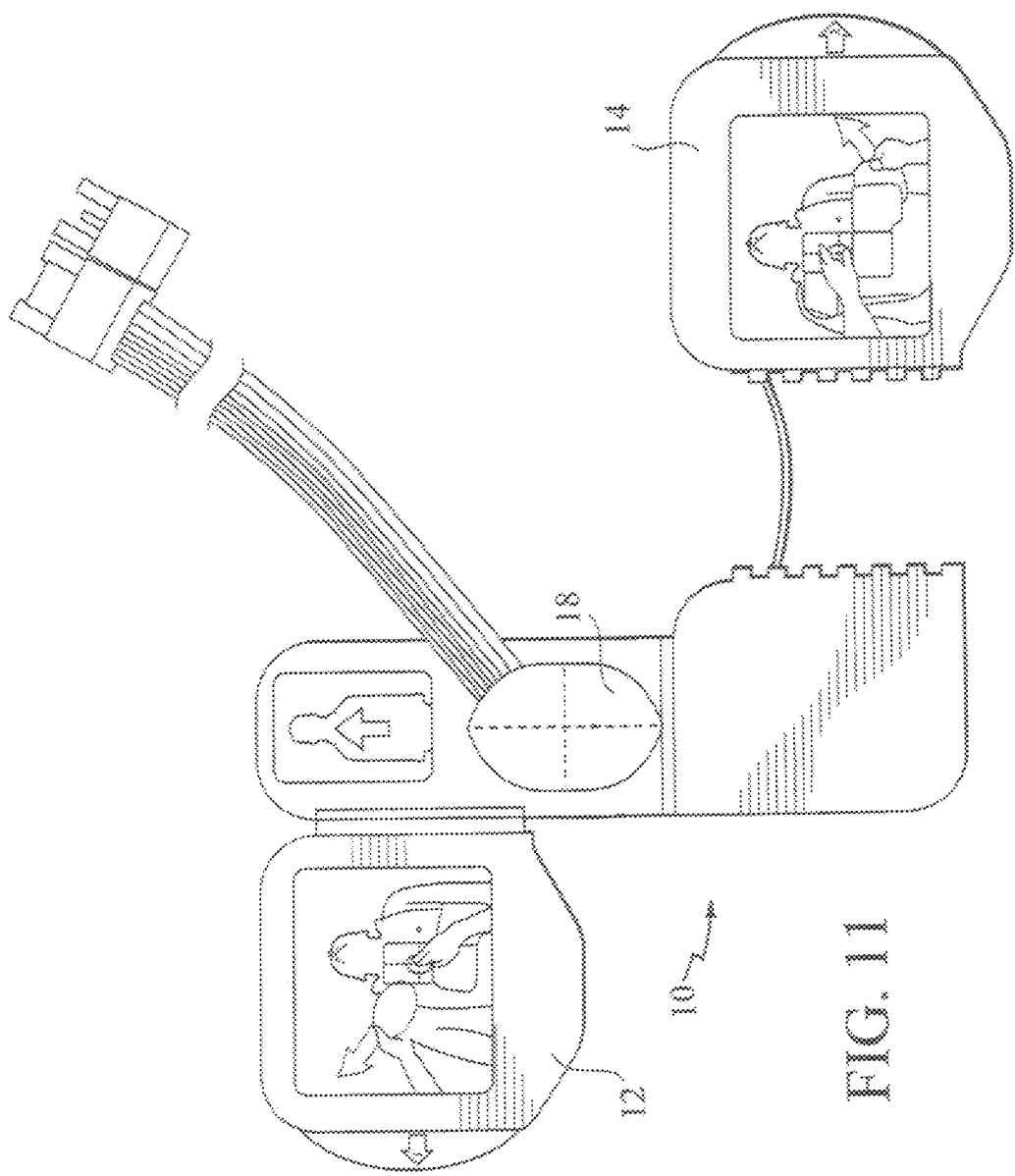

MOBILE DEVICE CONTROL

CLAIM OF PRIORITY

This application claims priority under 35 USC § 119 to U.S. patent application Ser. No. 14/036,503, file on Sep. 25, 2013 and entitled Mobile Device Control, the entire contents of which are hereby incorporated by reference.

TECHNICAL FIELD

This invention relates to resuscitation systems incorporating defibrillation therapy and resuscitation prompts.

BACKGROUND

Resuscitation can generally include clearing a patient's airway, assisting the patient's breathing, chest compressions, and defibrillation.

The American Heart Association's Basic Life Support for Health Care Providers textbook provides a flow chart at page 4-14 of Chapter 4 that lists the steps of airway clearing, breathing, and circulation (known as A, B, and C), for situations in which there is no defibrillator readily accessible to the rescuer.

Defibrillation (sometimes known as step D) can be performed with the use of an automatic external defibrillator (AED) Most automatic external defibrillators are actually semi-automatic external defibrillators (SAED), which require a clinician to press a start button, after which the defibrillator analyzes the patient's condition and provides a shock to the patient if the electrical rhythm is shockable and waits for user intervention before any subsequent shock. Fully automatic external defibrillators, on the other hand, do not wait for user intervention before applying subsequent shocks. As used below, automatic external defibrillators (AED) include semi-automatic external defibrillators (SAED).

Both types of defibrillators typically provide an oral stand clear warning before the application of each shock, and then the clinician is expected to stand clear of the patient and may be required to press a button indicating that the clinician is standing clear of the patient. The controls for automatic external defibrillators are typically located on a resuscitation control box.

AEDs are used typically by trained providers such as physicians, nurses, fire department personnel, and police officers. There might be one or two people at a given facility that has an AED who have been designated for defibrillation resuscitation before an ambulance service arrives. The availability of on-site AEDs along with rescuers trained to operate them is important because if the patient experiences a delay of more than 4 minutes before receiving a defibrillation shock the patient's chance of survival can drop dramatically. Many large cities and rural areas have low survival rates for defibrillation because the ambulance response time is slow, although many suburbs have higher survival rates because of the faster ambulance response time due to lack of traffic and availability of hospitals and advanced life support.

Trained lay providers are a new group of AED operators, but they rarely have opportunities to defibrillate. For example, spouses of heart attack victims may become lay providers, but these lay providers can be easily intimidated by an AED during a medical emergency. Consequently, such lay providers can be reluctant to purchase AEDs, or might tend to wait for an ambulance to arrive rather than use an available AED, out of concern that the lay provider might do something wrong.

There are many different kinds of heart rhythms, some of which are considered shockable and some of them are not. For example, a normal rhythm is considered non-shockable, and there are also many abnormal non-shockable rhythms. There are also some abnormal non-viable non-shockable, which means that the patient cannot remain alive with the rhythm, but yet applying shocks will not help convert the rhythm.

As an example of a non-shockable rhythm, if a patient experiences asystole, the heart will not be beating and application of shocks will be ineffective. Pacing is recommended for asystole, and there are other things that an advanced life support team can do to assist such patient, such as the use of drugs. The job of the first responder is simply to keep the patient alive, through the use of CPR and possibly defibrillation, until an advanced life support team arrives. Bradycardias, during which the heart beats too slowly, are non-shockable and also possibly non-viable. If the patient is unconscious during bradycardia, it can be helpful to perform chest compressions until pacing becomes available. Electro-mechanical dissociation (EMD), in which there is electrical activity in the heart but it is not making the heart muscle contract, is non-shockable and non-viable, and would require CPR as a first response. Idio-ventricular rhythms, in which the normal electrical activity occurs in the ventricles but not the atria, can also be non-shockable and non-viable (usually, abnormal electrical patterns begin in the atria). Idio-ventricular rhythms typically result in slow heart rhythms of 30 or 40 beats per minute, often causing the patient to lose consciousness. The slow heart rhythm occurs because the ventricles ordinarily respond to the activity of the atria, but when the atria stop their electrical activity, a slower, backup rhythm occurs in the ventricles.

The primary examples of shockable rhythms, for which a first responder should perform defibrillation, include ventricular fibrillation, ventricular tachycardia, and ventricular flutter.

After using a defibrillator to apply one or more shocks to a patient who has a shockable electrical rhythm, the patient may nevertheless remain unconscious, in a shockable or non-shockable rhythm. The rescuer may then resort to chest compressions. As long as the patient remains unconscious, the rescuer can alternate between use of the defibrillator (for analyzing the electrical rhythm and possibly applying a shock) and performing cardio-pulmonary resuscitation (CPR).

CPR generally involves a repeating pattern of chest compressions followed by a pause. CPR is generally ineffective against abnormal rhythms, but it does keep some level of blood flow going to the patient's vital organs until an advanced life support team arrives. It is difficult to perform CPR over an extended period of time. Certain studies have shown that over a course of minutes, rescuers tend to perform chest compressions with less-than-sufficient strength to cause an adequate supply of blood to flow to the brain. CPR prompting devices can assist a rescuer by prompting each chest compression and breath.

PCT Patent Publication No. WO 99/24114, filed by Heartstream, Inc., discloses an external defibrillator having PCR and ACLS (advanced cardiac life support) prompts.

SUMMARY

In a general aspect, a system includes a processor coupled to a memory, the processor and memory configured to determine a proficiency level of a user of a rescue application based on stored data indicative of the user's history of use of the rescue application, select a level of operation for the rescue application. The rescue application is executed on a mobile device and configured to control operation of a AED. Each of multiple levels of operation for the rescue application allows the user a different degree of control over the operation of the AED The processor and memory are configured to present, to the user, a set of instructions associated with the selected level of operation. A different set of instructions is associated with each of the multiple levels. The processor and memory are configured to enable control of the AED according to the selected levels of operation.

In a general aspect, a system includes a processor coupled to a memory, the processor and memory configured to determine a proficiency level of a user of a rescue application based on stored data indicative of the user's proficiency level, and based on the user's proficiency level, select a level of operation for the rescue application. The rescue application is executed on a mobile device and configured to control operation of an AED. Each of multiple levels of operation for the rescue application allows the user a different degree of control over the operation of the AED. The processor and memory are configured to present, to the user, a set of instructions associated with the selected level of operation. A different set of instructions is associated with each of the multiple levels. The processor and memory are configured to enable control of the AED according to the selected levels of operation.

In a general aspect, a system includes a processor coupled to a memory, the processor and memory configured to, based on a proficiency level of a user of a rescue application, select a level of operation for the rescue application. The rescue application is executed on a mobile device and configured to control operation of a treatment unit. The processor and memory are configured to enable control of the treatment unit according to the selected level of operation.

Embodiments can include one or more of the following features.

Each of multiple levels of operation allows the user a different degree of control over the operation of the treatment unit.

The treatment unit includes an AED

The processor and memory are is configured to, based on the level of operation, select a particular set of instructions from multiple sets of instructions to present to the user.

The processor and memory are configured to receive data about a patient being treated by the treatment unit. The processor and memory are configured to select at least some of the data for display on a display interface based on the level of operation. In some cases, the data is received from a multiple lead ECG.

The processor and memory are configured to receive an indication to execute the rescue application in either a rescue mode or a training mode. In some cases, when the rescue application is executed in training mode, enabling control of the treatment unit includes enabling simulation of the operation of the treatment unit. In some cases, when the rescue application is executed in rescue mode, enabling control of the treatment unit includes establishing a connection with an AED; and sending a control signal to the AED.

The proficiency level of the user is based on the user's history of using the rescue application.

The processor and memory are configured to increase the user's proficiency level when the user satisfies a metric associated with the rescue application.

The memory is configured to store data indicative of the user's history of using the rescue application. The processor and memory are configured to, based on the stored data, determine when the user has satisfied the metric. In some cases, the metric includes a metric associated with a particular one of the levels of operation of the rescue application.

Enabling control of the treatment unit includes automatically controlling the treatment unit.

Enabling control of the treatment unit includes controlling the operation of the treatment unit according to a command received from the user.

Enabling control of the treatment unit includes controlling the treatment unit to analyze a condition of a patient, to deliver a shock to the patient, or both.

In a general aspect, a computer readable medium stores instructions for causing a computing system to, based on a proficiency level of a user of a rescue application, select a level of operation for the rescue application; and enable control of the treatment unit according to the selected level of operation. The rescue application is executed on a mobile device and configured to control operation of a treatment unit.

Embodiments can include one or more of the following features.

Each of multiple levels of operation allows the user a different degree of control over the operation of the treatment unit.

The treatment unit includes an AED

The instructions cause the computing system to, based on the level of operation, select a particular set of instructions from multiple sets of instructions to present to the user.

The instructions cause the computing system to receive data about a patient being treated by the treatment unit; and select at least some of the data for display on a display interface based on the level of operation. In some cases, the data is received from a multiple lead ECG.

The instructions cause the computing system to receive an indication to execute the rescue application in either a rescue mode or a training mode. In some cases, when the rescue application is executed in training mode, enabling control of the treatment unit includes enabling simulation of the operation of the treatment unit. In some cases, when the rescue application is executed in rescue mode, enabling control of the treatment unit includes establishing a connection with an AED; and sending a control signal to the AED.

The proficiency level of the user is based on the user's history of using the rescue application.

The instructions cause the computing system to increase the user's proficiency level when the user satisfies a metric associated with the rescue application. In some cases, the instructions cause the computing system to store data indicative of the user's history of using the rescue application; and based on the stored data, determine when the user has satisfied the metric. In some cases, the metric includes a metric associated with a particular one of the levels of operation of the rescue application.

The instructions for causing the computing system to enable control of the treatment unit include instructions for causing the computing system to automatically control the treatment unit.

The instructions for causing the computing system to enable control of the treatment unit include instructions for causing the computing system to control the operation of the treatment unit according to a command received from the user.

The instructions for causing the computing system to enable control of the treatment unit include instructions for causing the computing system to control the treatment unit to analyze a condition of a patient, to deliver a shock to the patient, or both.

In a general aspect, a method includes determining a proficiency level of a user of a rescue application based on stored data indicative of the user's proficiency level. The rescue application is executed on a mobile device and configured to control operation of a AED The method includes, based on the user's proficiency level, selecting a level of operation for the rescue application. Each of multiple levels of operation for the rescue application allows the user a different degree of control over the operation of the AED. The method includes presenting, to the user, a set of instructions associated with the selected level of operation, wherein a different set of instructions is associated with each of the multiple levels; and enabling control of the AED according to the selected levels of operation.

The techniques described herein can have one or more of the following advantages. Providing control of a treatment unit, such as an AED, from a mobile computing device is convenient and allows users to deliver rescue treatments through a familiar interface. Users can practice treatment delivery using the mobile computing device as a simulator to gain experience outside of real emergency situations. Mobile computing devices can offer capabilities for powerful control of AEDs and other treatment and monitoring techniques. The capabilities that are accessible to a given user are tailored to the user's level of experience, thus helping to ensure that the user is provided with tools to deliver safe and effective treatment to a patient.

A portable ECG package allows medical personnel to carry around complex multiple lead ECG equipment, e.g., a 12-lead ECG, without the danger of damaging the ECG electrodes or tangling the ECG cables.

The details of one or more embodiments are set forth in the accompanying drawings and the description below. Other features and advantages will be apparent from the description, drawings, and claims.

BRIEF DESCRIPTION OF THE DRAWINGS

FIG. 11 is a drawing of the defibrillation electrode assembly of another alternative.

DETAILED DESCRIPTION

Figure 1:
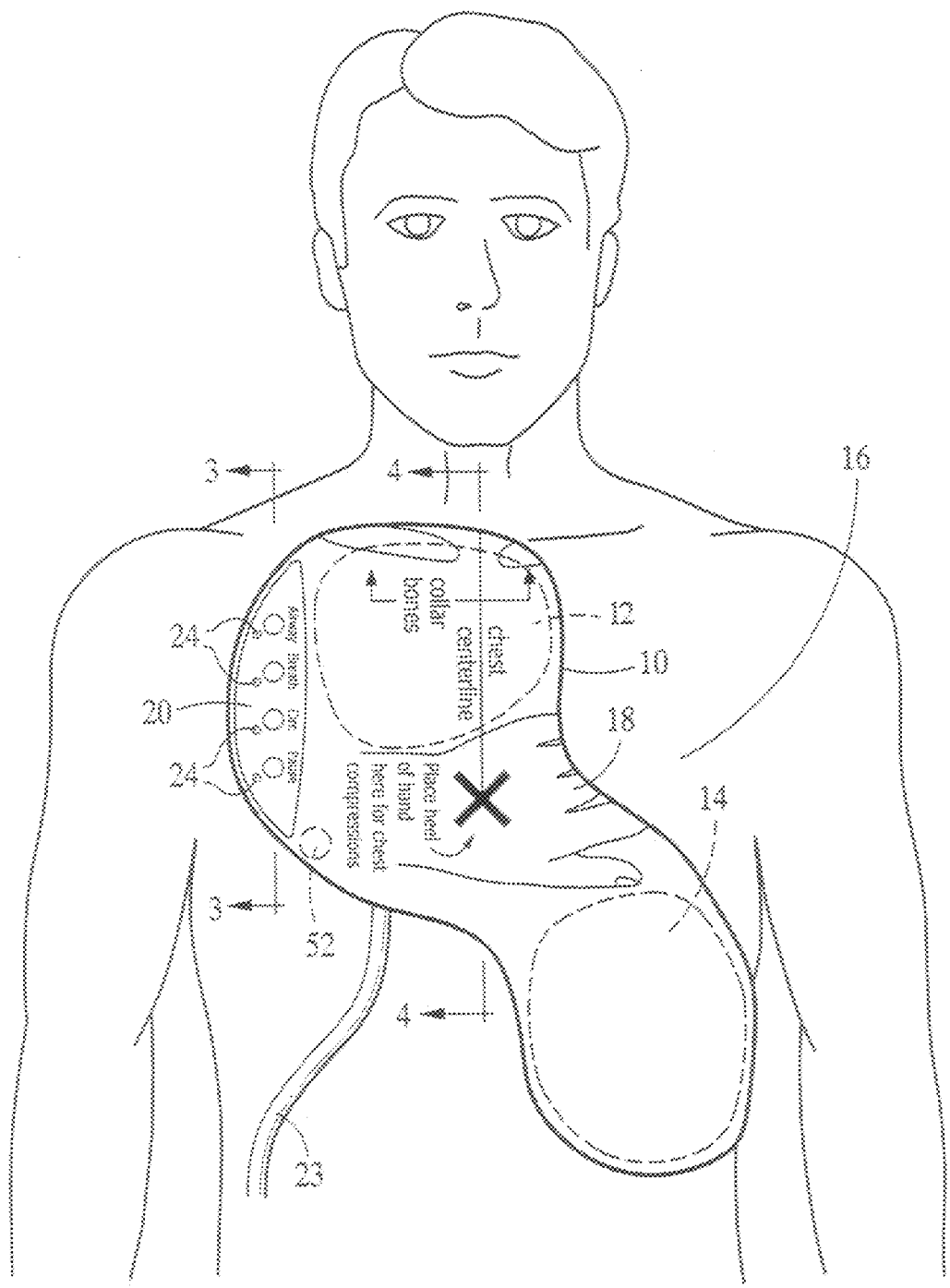
FIG. 1 is a drawing of a defibrillation electrode pad according to the invention, positioned over the chest of a patient.

With reference to FIG. 1, a defibrillation electrode pad 10, which includes high-voltage apex defibrillation electrode 12 and high-voltage sternum defibrillation electrode 14, is placed on the patient's chest 16 and includes a region 18 on which a user may press to perform CPR. Legends on pad 10 indicate proper placement of the pad with respect to the patient's collarbones and the chest centerline and the proper placement of the heel of the rescuer's hand.

A low-profile button panel 20 is provided on the electrode assembly. Button panel 20 has buttons 22, including buttons A (Airway Help), B (Breathing Help), C (Circulation Help) and PAUSE, and may also include adjacent light emitting diodes (LEDs) 24 that indicate which button has been most recently pressed. Button panel 20 is connected by a cable 23 to a remote resuscitation control box 26, shown in FIG. 2. Button panel 20 provides rigid support underneath buttons A, B, C, and PAUSE against which the switches can be pushed in order to ensure good switch closure while the electrode rests on a patient. Button panel 20 includes components that make electrical contact with silver/silver-chloride electrical circuit components screen-printed on a polyester base of defibrillation electrode pad 10, as is described in detail below.

A pulse detection system based on shining light through the patient's vascular bed, e.g., a pulse oximetry system 52, is incorporated into defibrillation electrode pad 10. Pulse oximetry system 52 includes a red light-emitting diode, a near-infrared light-emitting diode, and a photodetector diode (see FIG. 5) incorporated into defibrillation electrode pad 10 in a manner so as to contact the surface of the patient's chest 16. The red and near-infrared light-emitting diodes emit light at two different wavelengths, which is diffusely scattered through the patient's tissue and detected by the photodetector diode. The information obtained from the photodetector diode can be used to determine whether the patient's blood is oxygenated, according to known noninvasive optical monitoring techniques.

In another implementation, the pulse detection system is a phonocardiogram system for listening to the sound of the victim's heart, rather than a pulse oximetry system. The phonocardiogram system includes a microphone and an amplifier incorporated within the electrode pad. Because a heart sound can be confused with microphone noise, the signal processing that must be performed by the microprocessor inside the control box will be more difficult in connection with a phonocardiogram system than in connection with a pulse oximetry system. Nevertheless, there are programs available that can enable the microprocessor to determine whether an ECG signal is present as opposed to microphone noise.

Pulse oximetry is a well-developed, established technology, but it requires good contact between the light sources and the victim's skin so that light can shine down into the victim's vascular bed. Many victims have lots of chest hair, which can interfere with good contact. It may be desirable for different types of electrode pads to be available at a given location (one having a pulse oximetry system and one having a phonocardiogram system) so that a rescuer can select an appropriate electrode pad depending on the nature of the victim.

In another implementation, instead of providing a low-profile button panel, a button housing can be provided that is affixed to an edge of the defibrillation electrode. The housing may be in the form of a clamshell formed of single molded plastic element having a hinge at an edge of the clamshell around which the plastic bends. The two halves of the clamshell can be snapped together around the electrode assembly.

The resuscitation control box (FIG. 2) includes an internal charge storage capacitor and associated circuitry including a microprocessor, an further includes off/on dial 28, and a "READY" button 30 that the rescuer presses immediately prior to application of a defibrillation shock in order to ensure that the rescuer is not in physical contact with the patient. The microprocessor may be a RISC processor such as a Hitachi SH-3, which can interface well with displays and keyboards, or more generally a processor capable of handling DSP-type (digital signal processing) operations.

The resuscitation control box has printed instructions 32 on its front face listing the basic steps A, B, and C for resuscitating a patient and giving basic instructions for positioning the defibrillation electrode pad on the patient. A speaker 32 orally prompts the user to perform various steps, as is described in detail below.

For example, the resuscitation control box instructs the user, by audible instructions and also through a display 34 on the resuscitation control box, to check the patient's airway and perform mouth-to-mouth resuscitation, and if the patient's airway is still blocked, to press the A (Airway Help) button on the button panel (FIG. 1), upon which the resuscitation control box gives detailed prompts for clearing the patient's airway. If the patient's airway is clear and the patient has a pulse but the patient does not breathe after initial mouth-to-mouth resuscitation, the resuscitation control box instructs the user press the B (Breathing Help) button, upon which the resuscitation control box gives detailed mouth-to-mouth resuscitation prompts. If, during the detailed mouth-to-mouth resuscitation procedure, the rescuer checks the patient's pulse and discovers that the patient has no pulse, the resuscitation control box instructs the user to press the C (Circulation Help) button.

During the circulation procedure, the resuscitation control box receives electrical signals from the defibrillation electrodes and determines whether defibrillation or CPR should be performed. If the resuscitation control box determines that defibrillation is desirable, the resuscitation control box instructs the user to press the "ready" button on the resuscitation control box and to stand clear of the patient. After a short pause, the resuscitation control box causes a defibrillation pulse to be applied between the electrodes. If at any point the resuscitation control box determines, based on the electrical signals received from the electrodes, that CPR is desirable, it will instruct the user to perform CPR.

Thus, the key controls for the system are on the electrodes attached to the patient rather than the resuscitation control box. This is important because it enables the rescuer to remain focused on the patient rather than the control box. The resuscitation control box gets its information directly from the electrodes and the controls on the electrodes.

The resuscitation control box can sense electrical signals from the patient's body during pauses between CPR compressions. Also, as is described below, a compression-sensing element, such as an accelerometer or other acceleration sensing element, or a force-sensing element is provided in the region of the defibrillation electrode pad on which the user presses to perform CPR. The purpose of the compression-sensing or force-sensing element is to allow the resuscitation control box to prompt the user to apply additional compression or force, or to prompt the user to cease CPR if the user is performing CPR at an inappropriate point in time.

Figure 4:
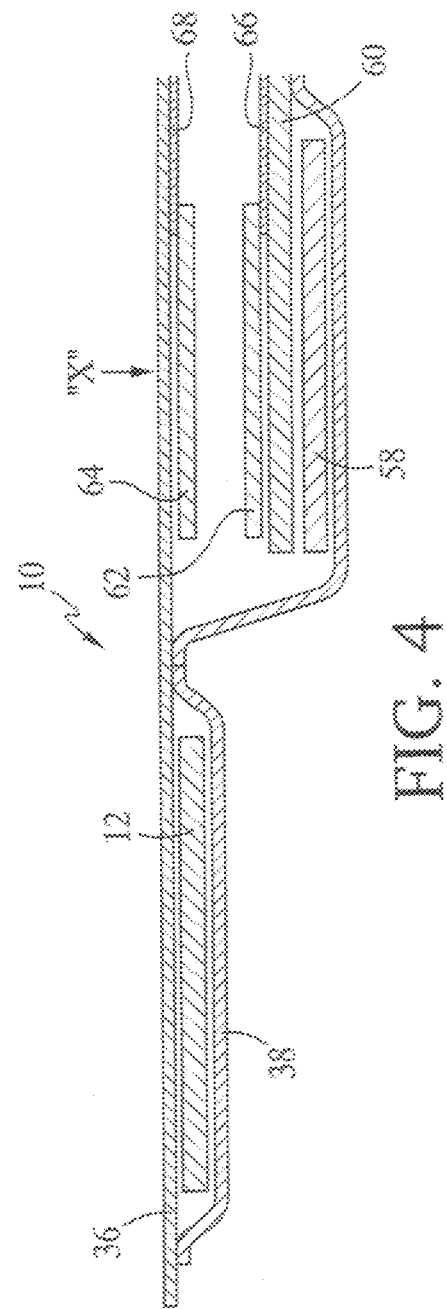
FIG. 4 is a cross-sectional drawing of the defibrillation pad of FIG. 1 taken along line 4-4.

Referring to FIG. 4, in one implementation, each electrode 12, 14 (only electrode 12 is shown) of defibrillation electrode pad 10 includes a polymer-based ink containing a silver/silver-chloride suspension, which is screen-printed on a polyester or plastic base 36. The ink is used to carry the defibrillation current. The screen-printing process first involves applying a resist layer to the polyester base 36. The resist layer is basically a loose mesh of nylon or the like, in which the holes have been filled in at some locations in the mesh. Then, the silver/silver-chloride ink is applied as a paste through the resist layer in a squeegee-like manner. The ink squeezes through the screen and becomes a solid layer. The ink may then be cured or dried. The silver/silver-chloride ink provides good conductivity and good monitoring capabilities.

Thus, the ink can be applied as pattern, as opposed to a solid sheet covering the entire polyester base. For example, U.S. Pat. No. 5,330,526 describes an electrode in which the conductive portion has a scalloped or daisy shape that increases the circumference of the conductive portion and reduces burning of the patient. A conductive adhesive gel 38 covers the exposed surface of each electrode.

In addition, electrical circuit components are also be screen printed on the base, in the same manner as flat circuit components of membrane-covered, laminated panel controls.

Figure 3:
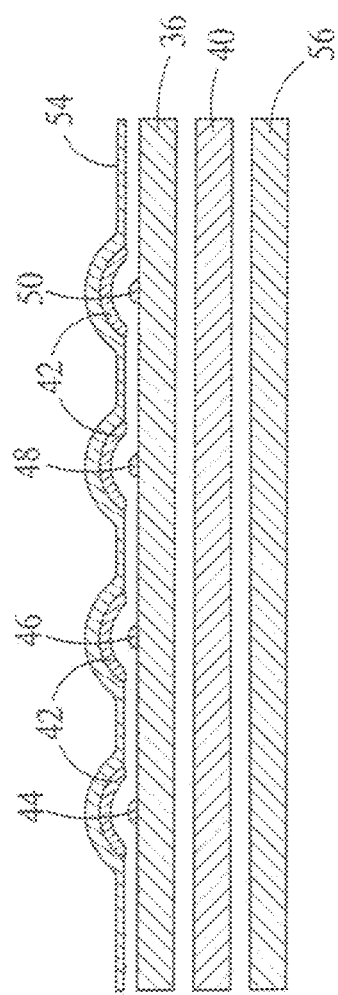
FIG. 3 is a cross-sectional drawing of the defibrillation electrode pad of FIG. 1 taken along line 3-3.

Referring to FIG. 3, a rigid piece 40 of hard plastic, such as PVC or polycarbonate, is laminated beneath substrate 36 and supports buttons A, B, C, and PAUSE. The rigid plastic piece 40 is glued onto substrate 36. Buttons A, B, C, and PAUSE consist of small metal dome snap-action switches that make contact between an upper conductive ink trace 42 and lower conductive ink traces 44, 46, 48, and 50. Buttons A, B, C, and PAUSE serve as controls that can be activated by the user that are physically located either on or immediately adjacent to the electrode assembly itself. Each of buttons A, B, C, and PAUSE may be associated with an adjacent light-emitting diode (LED). For example, LEDs may be glued, using conductive epoxy, onto silver/silver-chloride traces on substrate 36. An embossed polyester laminate layer 54 covers conductive ink trace 42 of buttons A, B, C, and PAUSE, and a foam layer 56 is laminated beneath rigid plastic piece 40.

Referring again to FIG. 4, defibrillation electrode pad 10 includes an extension piece that is placed directly over the location on the patient's body where the rescuer performs chest compressions. This extension piece includes substrate 36, and a semi-rigid plastic supporting member 58 laminated underneath substrate 36 that covers the chest compression area. Semi-rigid supporting member 58 provides somewhat less rigidity than rigid plastic piece 409 provided at the location of buttons A, B, C, and PAUSE (illustrated in FIG. 3).

In implementations having a force-sensing element, a polyester laminate 60, and a force-sensing resistor having two layers of carbon-plated material 62 and 64, are laminated between polyester substrate 36 and semi-rigid supporting member 58. A suitable construction of the force-sensing resistor is illustrated in the FSR Integration Guide & Evaluation Parts Catalog with Suggested Electrical Interfaces, from Interlink Electronics. The electrical contact between the two carbon-plated layers of material increases with increased pressure, and the layers of force-sensing resistive material can provide a generally linear relationship between resistance and force. Conductive ink traces 66 and 68 provide electrical connections to the two layers of the force-sensing resistor.

During chest compressions, the rescuer's hands are placed over the extension piece, and the force-sensing resistor of the extension piece is used to sense the force and the timing of the chest compressions. The force-sensing resistor provides information to the resuscitation control box so that the resuscitation control box can provide the rescuer with feedback if the rescuer is applying insufficient force. The resuscitation control box also provides coaching as to the rate at which CPR is performed. In certain situations, the resuscitation control box indicates to the rescuer that CPR should be halted because it is being performed at an inappropriate time, such as immediately prior to application of a defibrillation shock when the rescuer's hands should not be touching the patient, in which case the resuscitation control box will also indicate that the rescuer should stay clear of the patient because the patient is going to experience a defibrillation shock.

As is noted above, during CPR the rescuer pushes on the patient's chest through the extension piece in the vicinity of the electrodes. If the resuscitation control box were to perform analysis during the chest compressions, the chest compressions would be likely to affect the sensed electrical rhythm. Instead, during the pauses between sets of compressions (for example, the pause after every fifth chest compression), the resuscitation control box can perform an electrocardiogram (ECG) analysis. The resuscitation control box might discover, for example, that the patient who is undergoing CPR is experiencing a non-shockable rhythm such as bradycardia, in which case the CPR is required in order to keep the patient alive, but then the resuscitation control box may discover that the rhythm has changed to ventricular fibrillation in the midst of CPR, in which case the resuscitation control box would instruct the rescuer to stop performing CPR so as to allow the resuscitation control box to perform more analysis and possibly apply one or more shocks to the patient. Thus, the rescuer is integrated into a sophisticated scheme that allows complex combinations of therapy.

In another implementation, a compression-sensing element such as an accelerometer may be used in place of a force-sensing element. The accelerometer, such as a solid-state ADXL202 accelerometer, is positioned at the location where the rescuer performs chest compressions. In this implementation, the microprocessor obtains acceleration readings from the accelerometer at fixed time intervals such as one-millisecond intervals, and the microprocessor integrates the acceleration readings to provide a measurement of chest compression. The use of an accelerometer is based on the discovery that it is more important to measure how deeply the rescuer is compressing the chest than to measure how hard the rescuer is pressing. In fact, every victim's chest will have a different compliance, and it is important that the chest be compressed to a recommended depth in a normal sized adult regardless of the victim's chest compliance.

Figure 2:
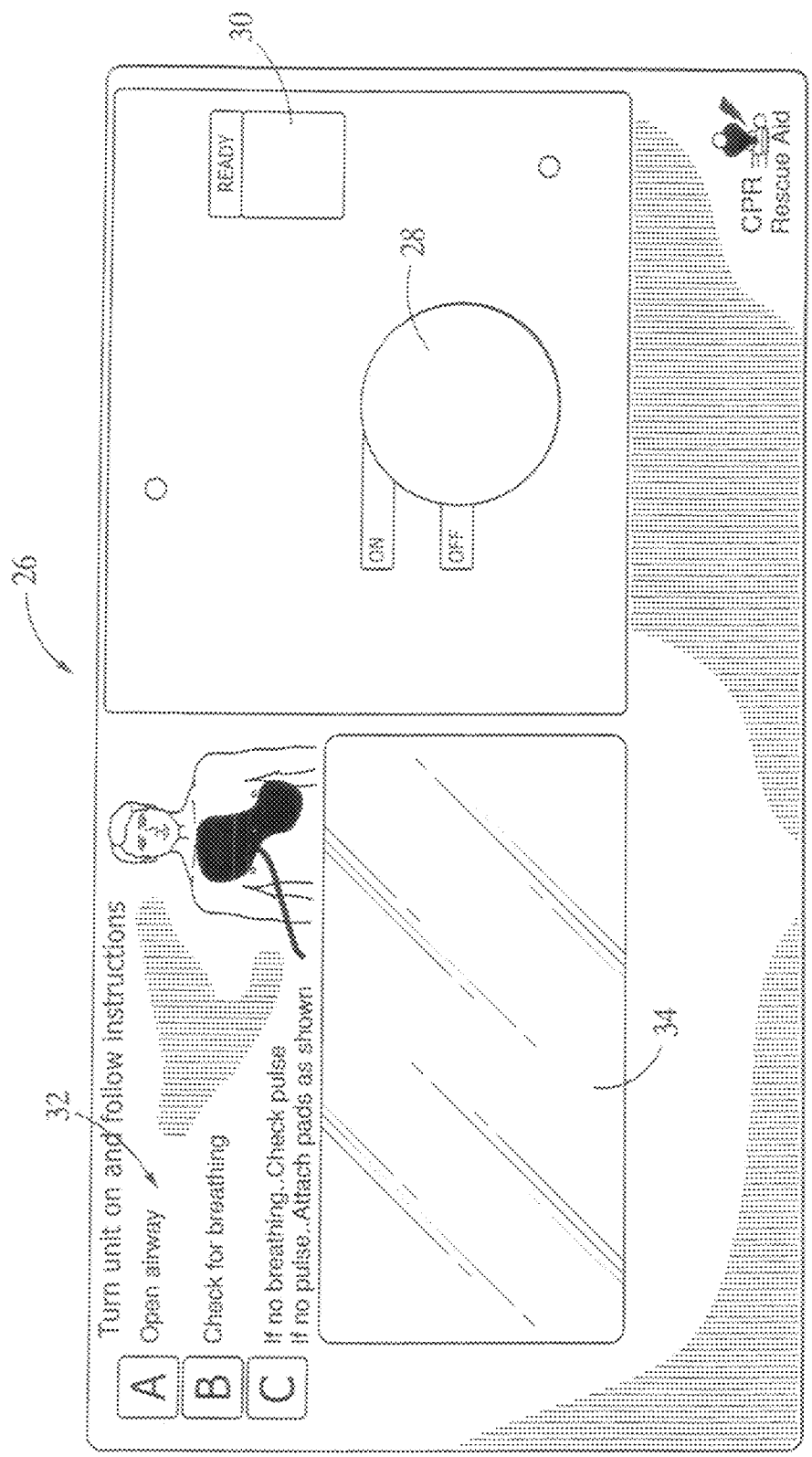
FIG. 2 is a view of the front display panel of a resuscitation control box according to the invention that houses electronic circuitry and provides audible and visual prompting.
Figure 5:
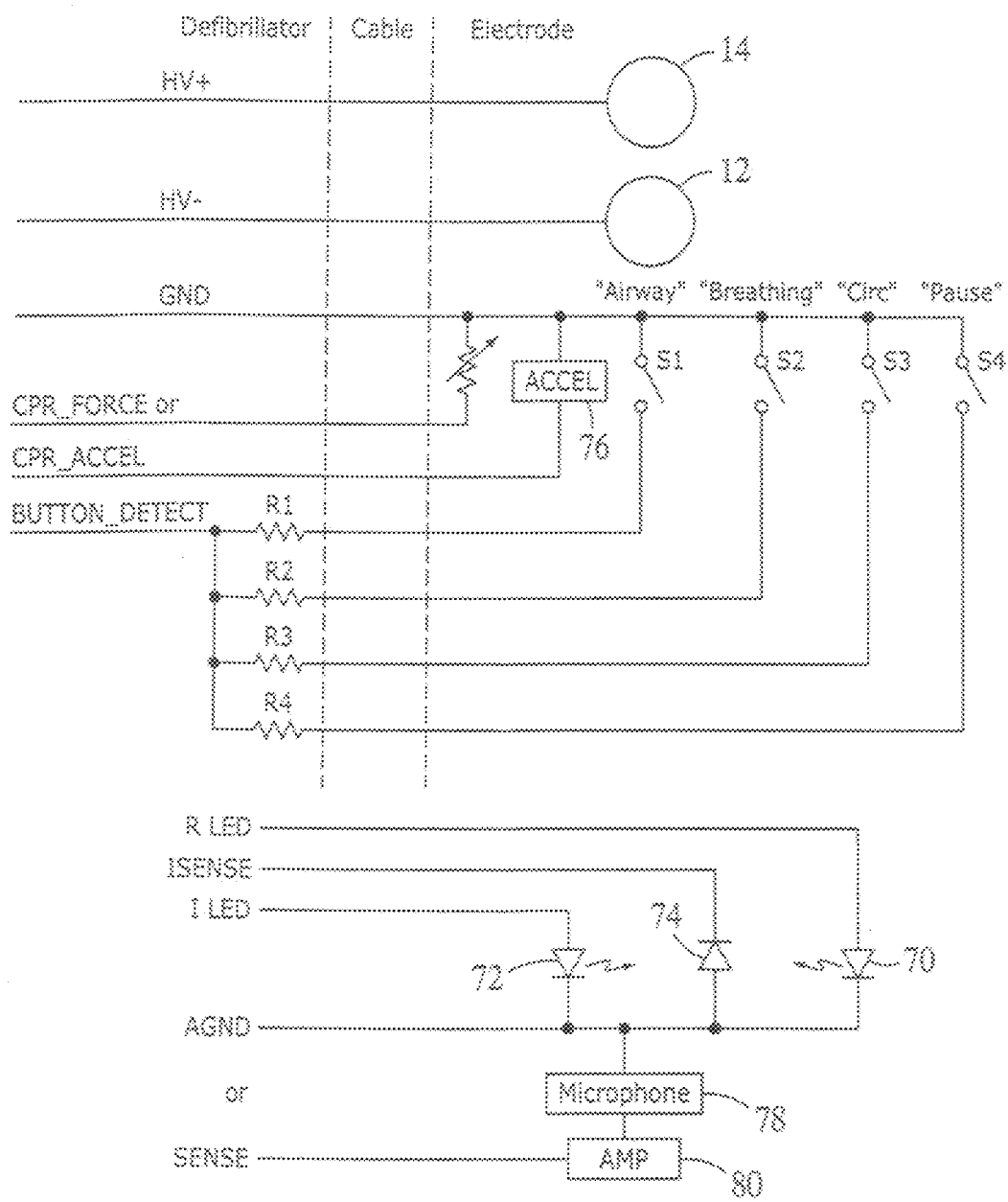
FIG. 5 is a circuit diagram illustrating the circuit interconnections between the defibrillation electrode pad of FIG. 1 and the resuscitation control box of FIG. 2.
Figure 6A:
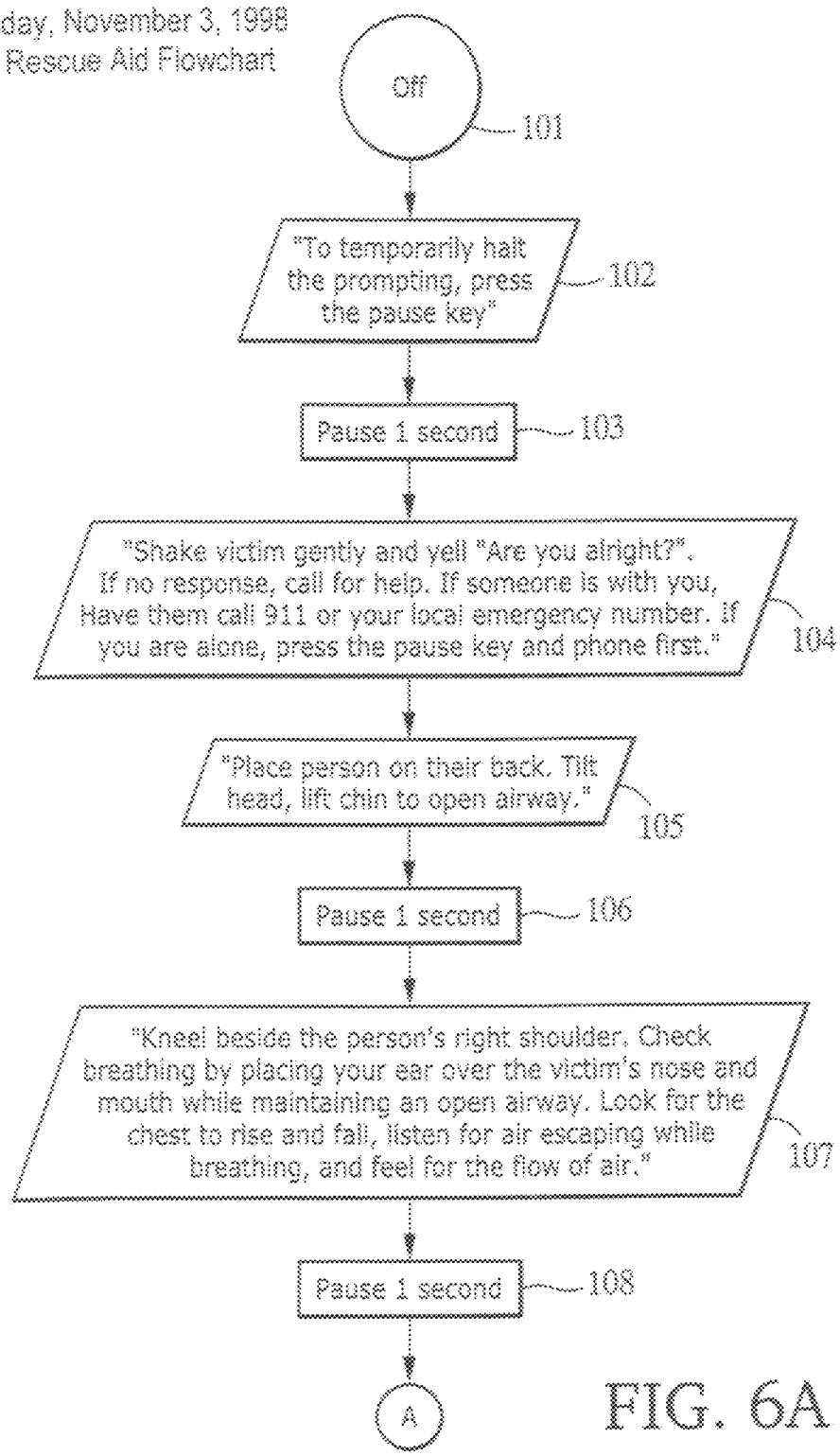
FIGS. 6A and 6B are a flowchart illustrating the initial routine of a resuscitation system according to the invention.
Figure 6B:
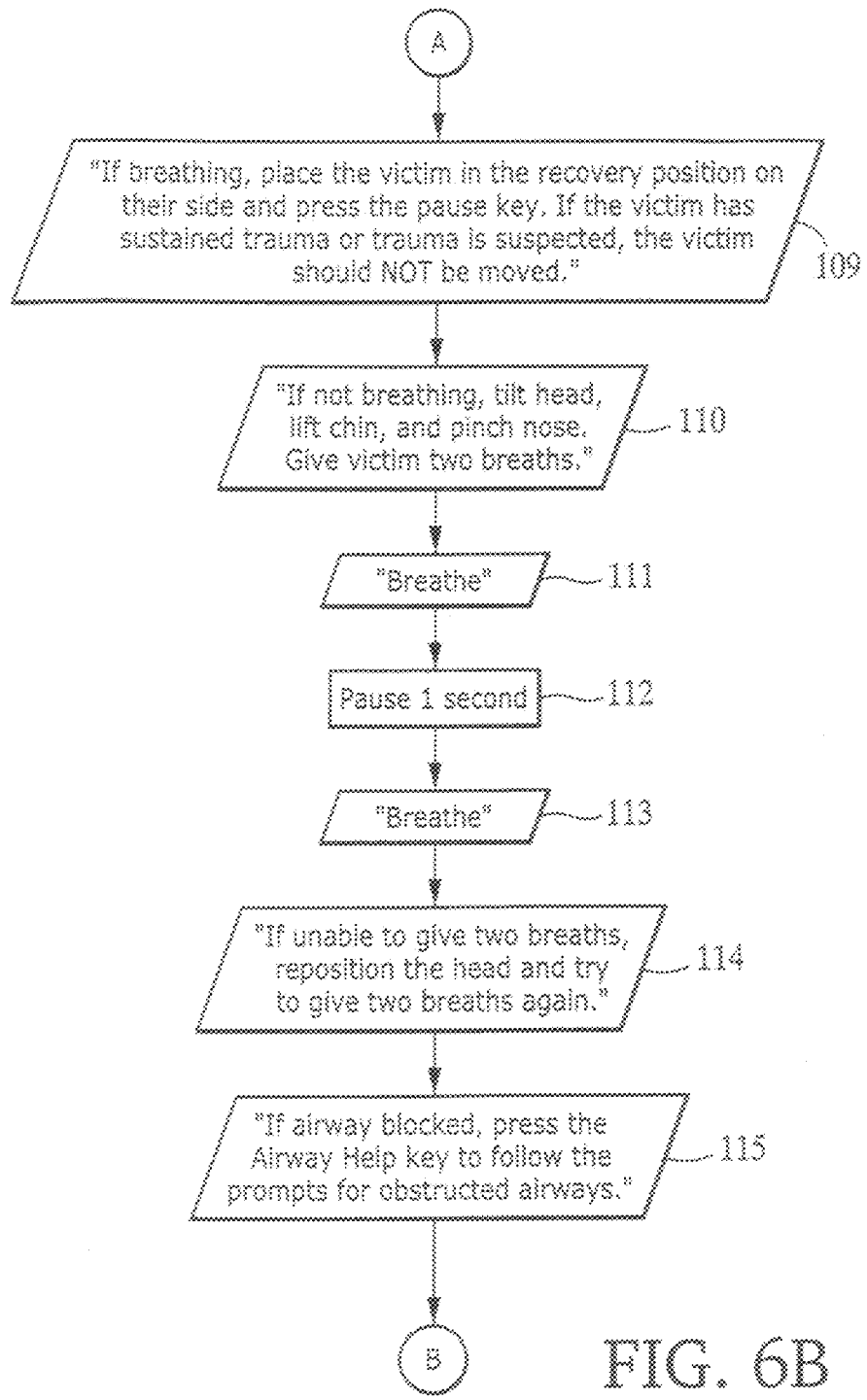
Figure 7A:
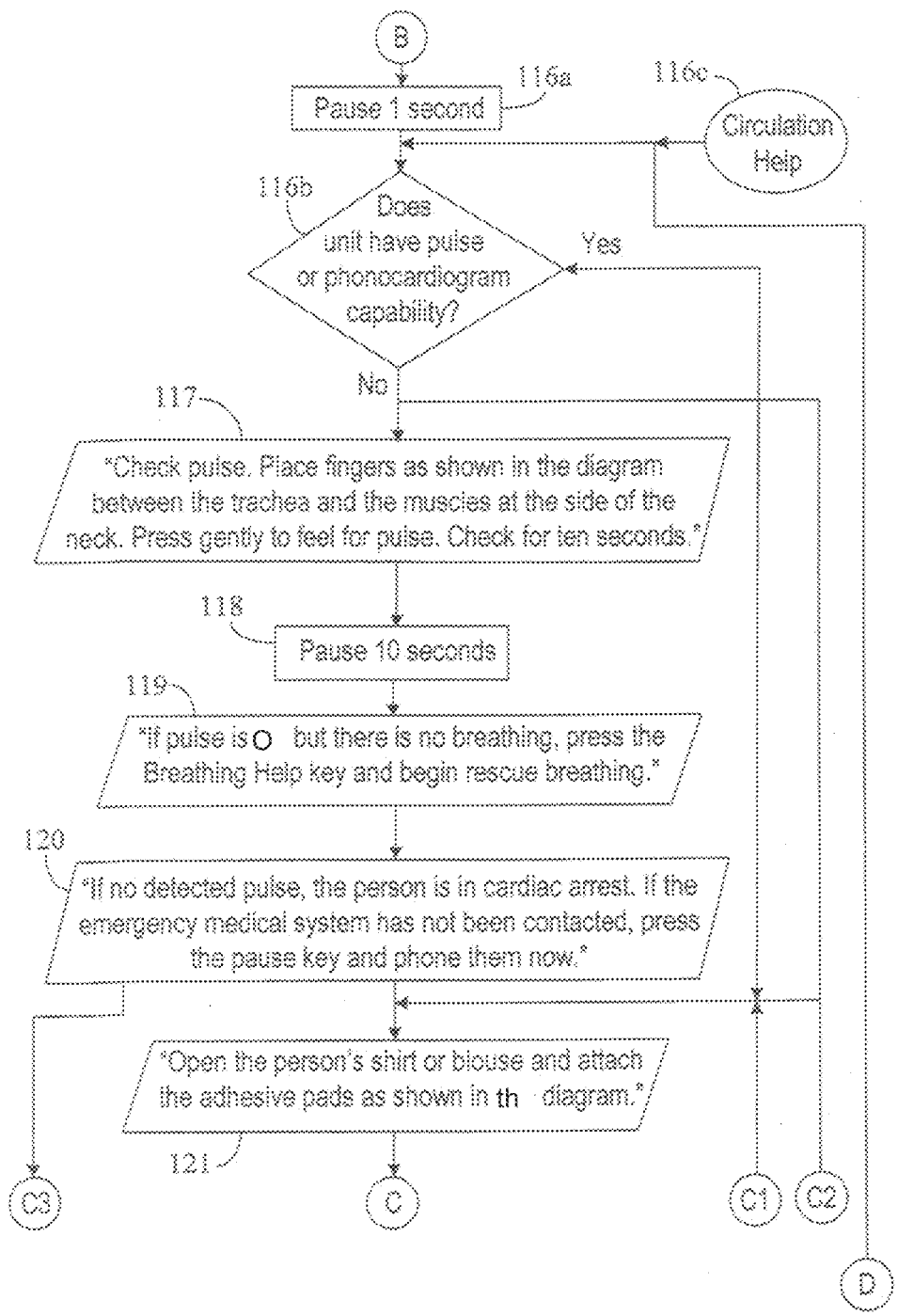
FIGS. 7A, 7B, and 7C are a flowchart illustrating the "circulation help" routine of the resuscitation system.
Figure 7B:
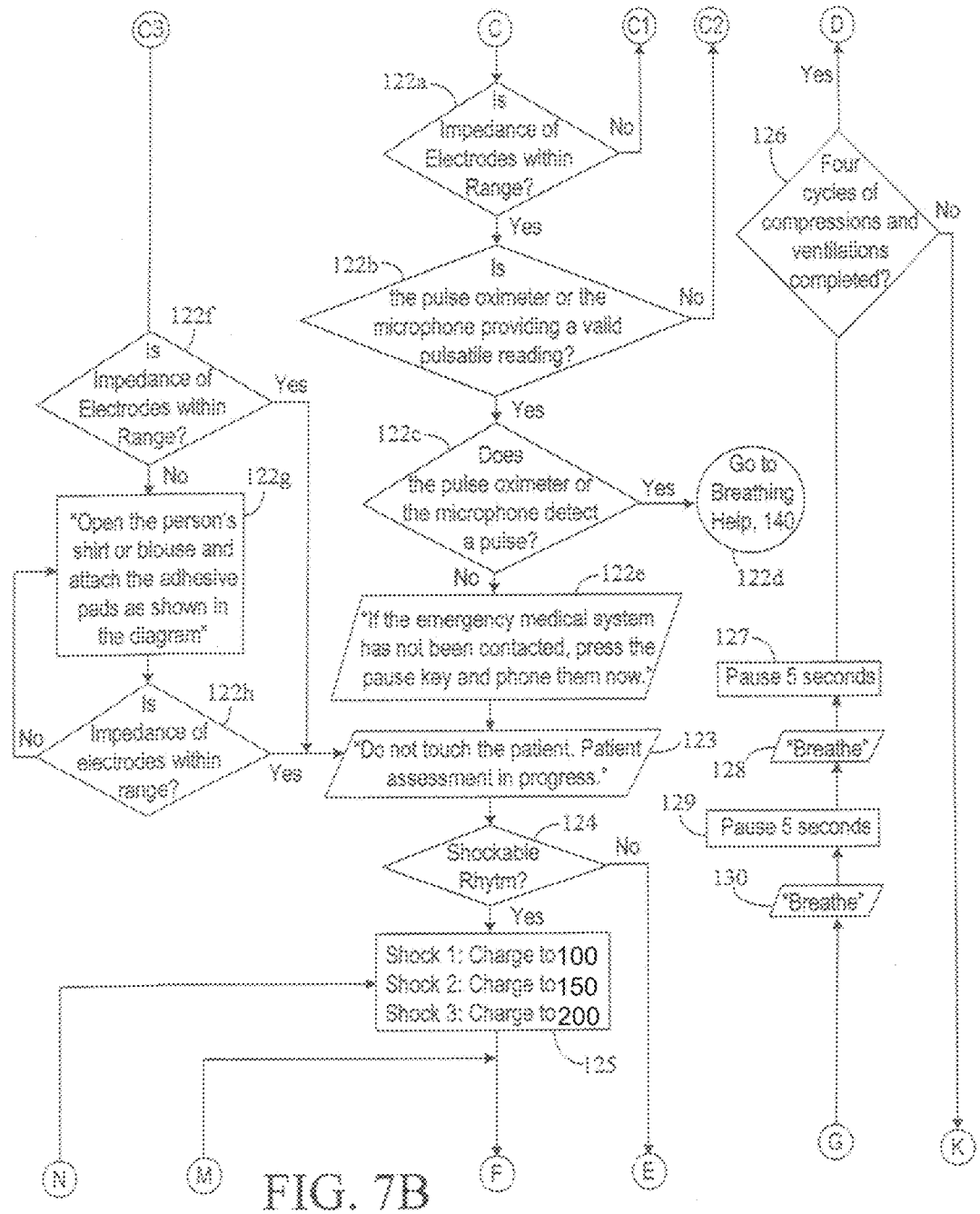
Figure 7C:
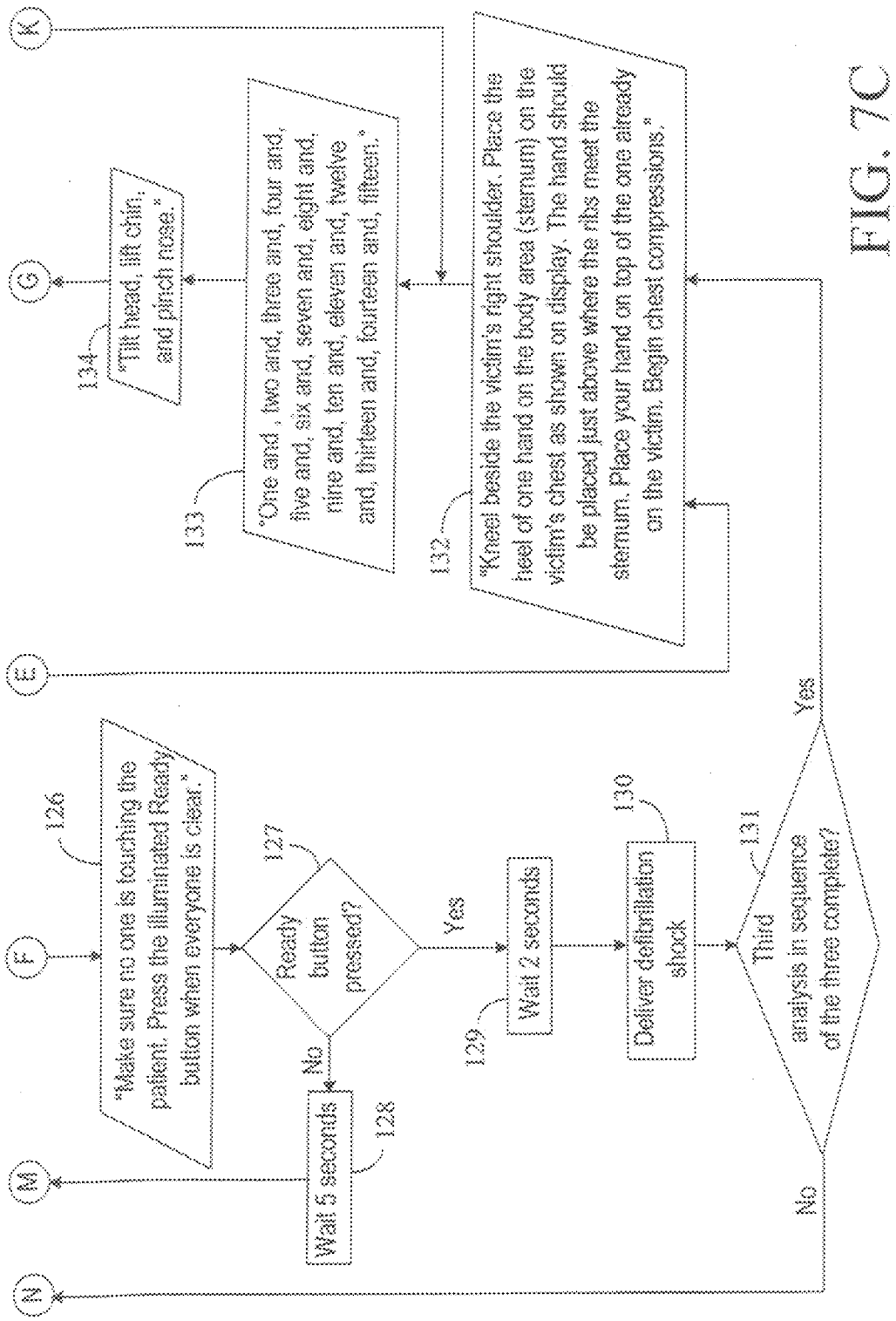

FIG. 5 is a circuit diagram illustrating the circuit interconnections between the defibrillation electrode pad of FIG. 1 through the cable to the resuscitation control box of FIG. 2. Sternum electrode 14 is connected to HV+ at the resuscitation control box, and apex electrode 12 is connected to HV−. A ground GND is connected to the upper conductive ink trace of buttons A, B, C, and PAUSE and to one of the layers of the force-sensing resistor. The other layer of the force-sensing resistor is connected to CPR_FORCE, and the lower conductive ink traces associated with buttons A, B, C, and PAUSE are connected to BUTTON_DETECT through resistors R1, R2, R3, and R4. As an alternative to the use of a force-sensing resistor, a compression-sensing accelerometer 76 may be employed, in which case CPR_FORCE is replaced by CPR_ACCEL connected to accelerometer 76. Red light-emitting diode 70, near-infrared light-emitting diode 72, and photodetector diode 74 of the pulse oximetry system are connected to RLED, ILED, and ISENSE respectively, as well as ground AGND. As an alternative to the use of a pulse oximetry system, a phonocardiogram system may be employed, in which case RLED, ILED, and ISENSE is replaced by SENSE connected to microphone 78 and amplifier 80.

FIGS. 6-9 illustrate the routine of the resuscitation system, which is based on steps A, B, and C (airway, breathing, and circulation). Because step C includes defibrillation as well as chest compressions, all of the aspects of resuscitation are tied together in one protocol (actually, if defibrillation were considered to be a step D distinct from step C, the sequence of steps would be A, B, D, C).

The first thing the rescuer must do upon arriving at the patient is to determine whether the patient is unconscious and breathing. The rescuer opens the patient's airway, administers breaths to the patient if the patient is not breathing, and checks to determine whether a pulse is present. If there is no pulse, rather than perform chest compressions as in standard CPR, the rescuer allows the resuscitation control box to analyze the patient's electrical rhythm, and if the resuscitation control box determines that the rhythm is shockable, the resuscitation control box causes one or more shocks to be applied to the patient, and then the rescuer performs chest compressions. Thus, there is provided a first response system that can keep the patient viable until an advanced life support time arrives to perform advanced techniques including pacing, further defibrillation, and drug therapy.

If the resuscitation control box determines that it should apply one or more defibrillation shocks to the patient, it is important that the rescuer not be anywhere near the patient when the shocks are applied to the patient. Prior to application of each shock, the resuscitation control box instructs the rescuer to please press the "ready" button when everybody is clear of the patient. The pressing of the "ready" button verifies that the rescuer's hands are off of the patient.

When the resuscitation control box detects a shockable rhythm, the resuscitation control box provides shocks of appropriate duration and energy (such as a sequence of shocks of increasing energy from 100 Joules to 150 Joules to the highest setting, 200 Joules, with the resuscitation control box performing analysis after each shock to determine whether another shock is required). If the defibrillation therapy is successful, the patient's rhythm is typically converted from ventricular fibrillation, ventricular tachycardia, or ventricular flutter to bradycardia, idio-ventricular rhythm, or asystole, all of which require CPR. It is rare to convert to a normal rhythm. Once the resuscitation control box has caused defibrillation shocks to be applied to the patient, the resuscitation control box automatically senses the patient's condition, and depending on the patient's condition will either prompt the responder to perform CPR or will not prompt the respond to perform CPR.

Defibrillation equipment can be somewhat intimidating to rescuers who are not medical professionals because the equipment can lead the rescuer to feel responsibility for having to save a loved one's life. It is important that the defibrillation equipment reduce this sense of responsibility. In particular, when the rescuer presses the "ready" button, rather than apply a shock immediately that will cause the patient's body to jump dramatically, the resuscitation control box will thank the rescuer and instruct the rescuer to remain clear of the patient and then wait for about two seconds (the resuscitation control box may describe this period to the rescuer as being an internal safety check, even if no substantial safety check is being performed). This process has an effect similar to a conversation that hands responsibility to the resuscitation control box, which makes the decision whether to apply the shock. Thus, the system maintains the rescuer safety features of a semi-automatic external defibrillator, because the rescuer must press the "ready" button before each shock, while appearing to operate more as a fully automatic external defibrillator because the time delay immediately prior to each shock leaves the rescuer with the impression that operation of the equipment is out of the hands of the rescuer. The use of CPR prompts in combination with the defibrillation also adds to the sense that the rescuer is simply following instructions from the resuscitation control box.

With reference to FIGS. 6-9, when the rescuer turns the resuscitation control box on (step 101), the resuscitation control box first informs the rescuer that the rescuer can temporarily halt prompting by pressing the PAUSE button (step 102), and then, after a pause, instructs the rescuer to check responsiveness of patient, and if the patient is non-responsive to call an emergency medical service (EMS) (steps 103, 104). The resuscitation control box then instructs the rescuer to check the patient's airway to determine whether the patient is breathing (steps 105-107).

After a pause, the resuscitation control box then instructs the rescuer that if the patient is breathing the patient should be placed on the patient's side, unless trauma is suspected, and that the rescuer should press the PAUSE button (steps 108-109). Then the resuscitation control box instructs the rescuer to perform mouth-to-mouth resuscitation if the patient is not breathing (steps 110-114). Then the resuscitation control box instructs the rescuer to press an Airway Help button A if the patient's airway is blocked, so that the resuscitation control box can give prompts for clearing obstructed airways (steps 115 of FIG. 6B and 147-158 of FIGS. 9A-9B).

Next, after a pause (step 116a), if the resuscitation control box does not include pulse oximetry or phonocardiogram capability (step 116b), the resuscitation control box instructs the rescuer to check the patient's pulse (step 117). After another pause, the resuscitation control box instructs the rescuer to press a Breathing Help button B if the patient's pulse is okay but the patient is not breathing, so that the resuscitation control box can give prompts for assisting the patient's breathing (steps 118 and 119 of FIG. 7A and 140-146 of FIG. 8). Light-emitting diodes adjacent the various buttons indicate which button has been pressed most recently (only one light remains on at a time). The resuscitation control box next prompts the rescuer to contact an emergency medical system (step 120) and to open the patient's shirt or blouse and attach the adhesive pads (steps 122f-122h).

If the resuscitation control box does include pulse oximetry or phonocardiogram capability (step and 116b), the resuscitation control box prompts the rescuer to open the patient's shirt or blouse and attach the adhesive pads (steps 121 and 122a). If the pulse oximetry or phonocardiogram system does not provide a valid pulsatile reading (step 122b), then the flow chart proceeds to step 117. If the pulse oximetry or phonocardiogram system does provide a valid pulsatile reading and detects a pulse (steps 122b and 122c), then the resuscitation control box begins the breathing help routine (steps 122d of FIG. 7B and step 140 of FIG. 8). If the pulse oximetry or phonocardiogram system does not detect a pulse, then the resuscitation control prompts the rescuer to contact an emergency medical system (step 122e), measures the impedance of the patient to determine whether it is within an acceptable range for application of shocks (step 123) and determines whether the patient's rhythm is shockable (steps 124). If the rhythm is shockable, the resuscitation control box causes a sequence of shocks to be applied to the patient, each shock requiring the rescuer first to press the "READY" button on the resuscitation control box (steps 124-131). After the last shock in the sequence, or if the rhythm is non-shockable, the resuscitation control box prompts the rescuer in CPR (steps 132-139). The flowchart then returns to step 117.

Figure 8:
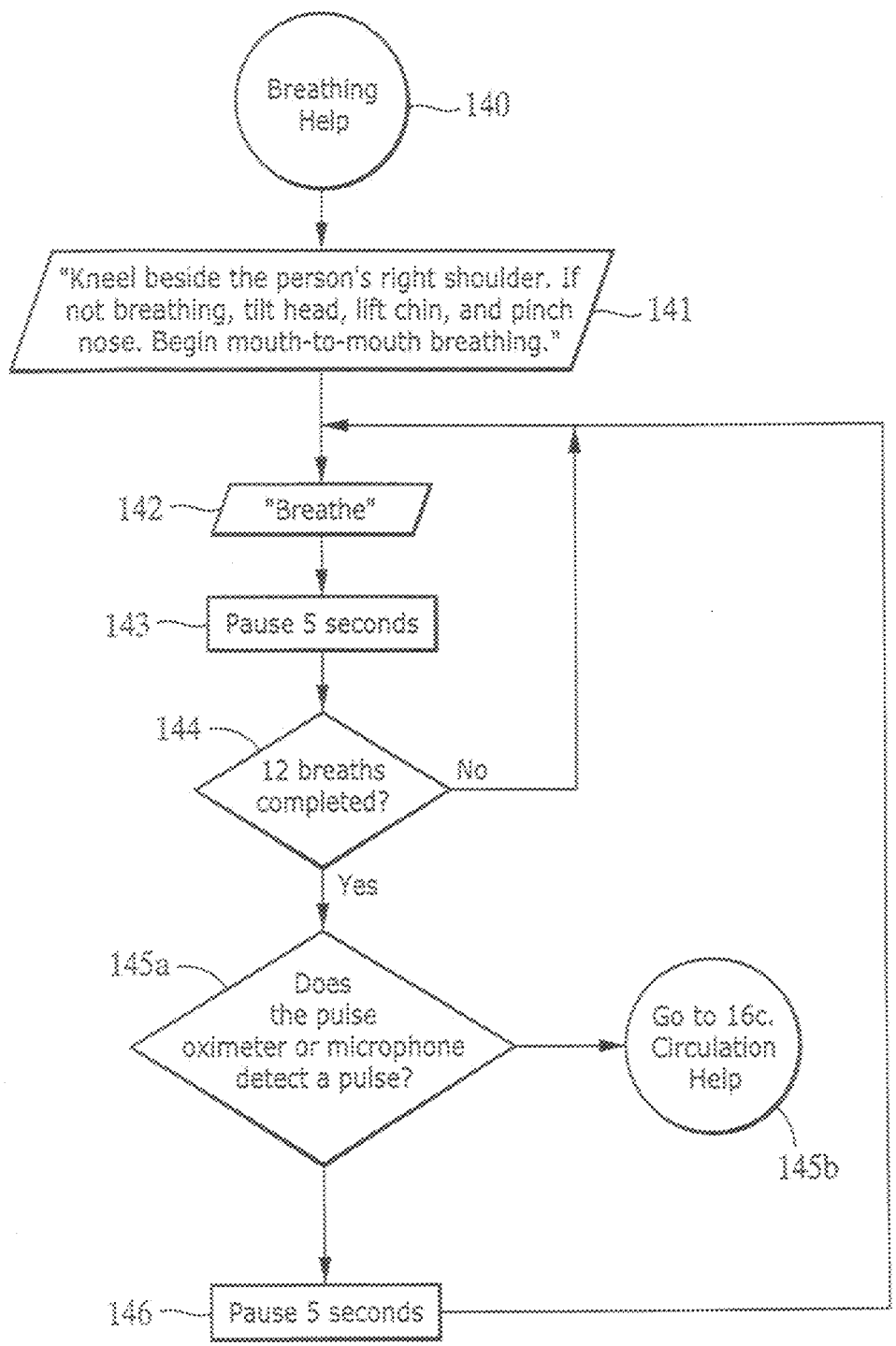
FIG. 8 is a flowchart illustrating the "breathing help" routine of the resuscitation system.
Figure 9A:
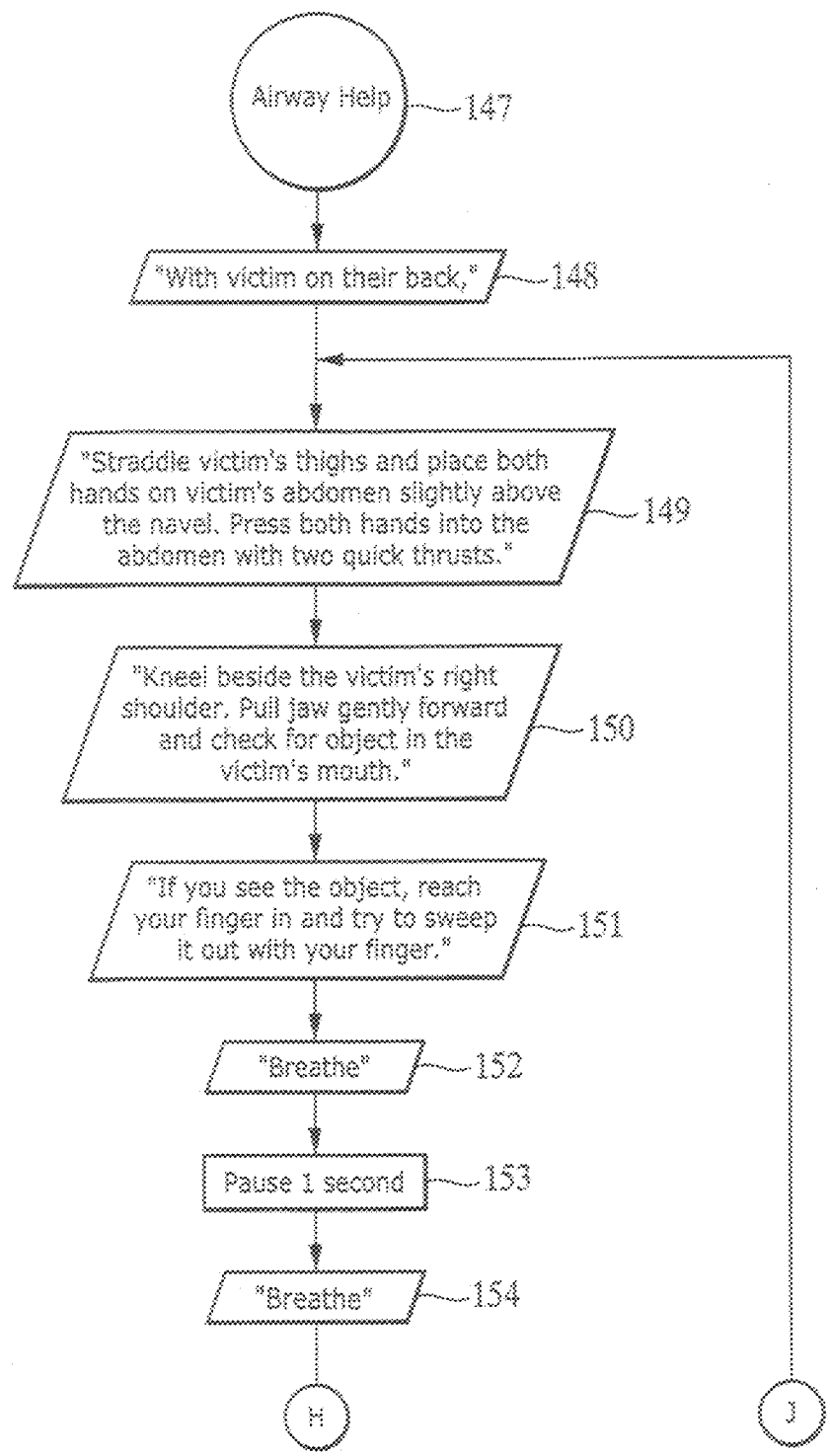
FIGS. 9A and 9B are a flowchart illustrating the "airway help" routine of the resuscitation system.
Figure 9B:
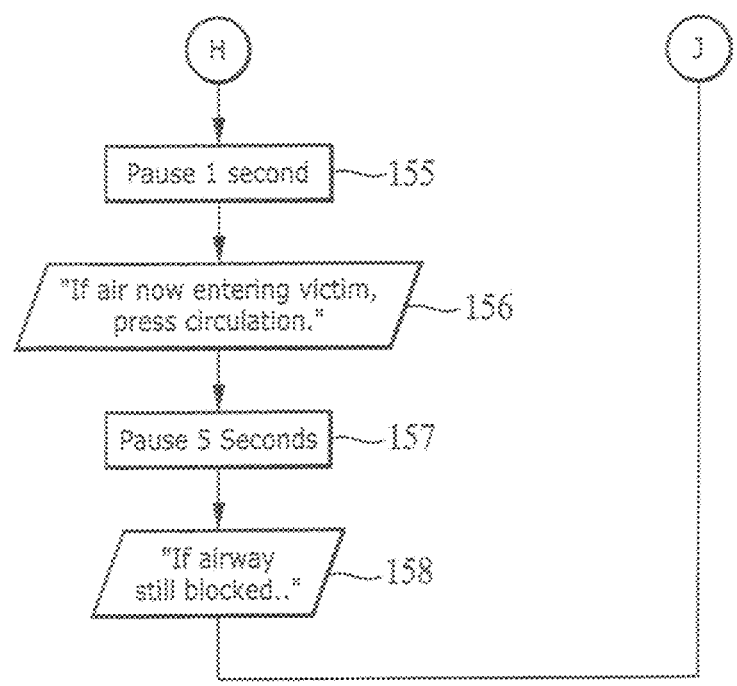
Figure 10:
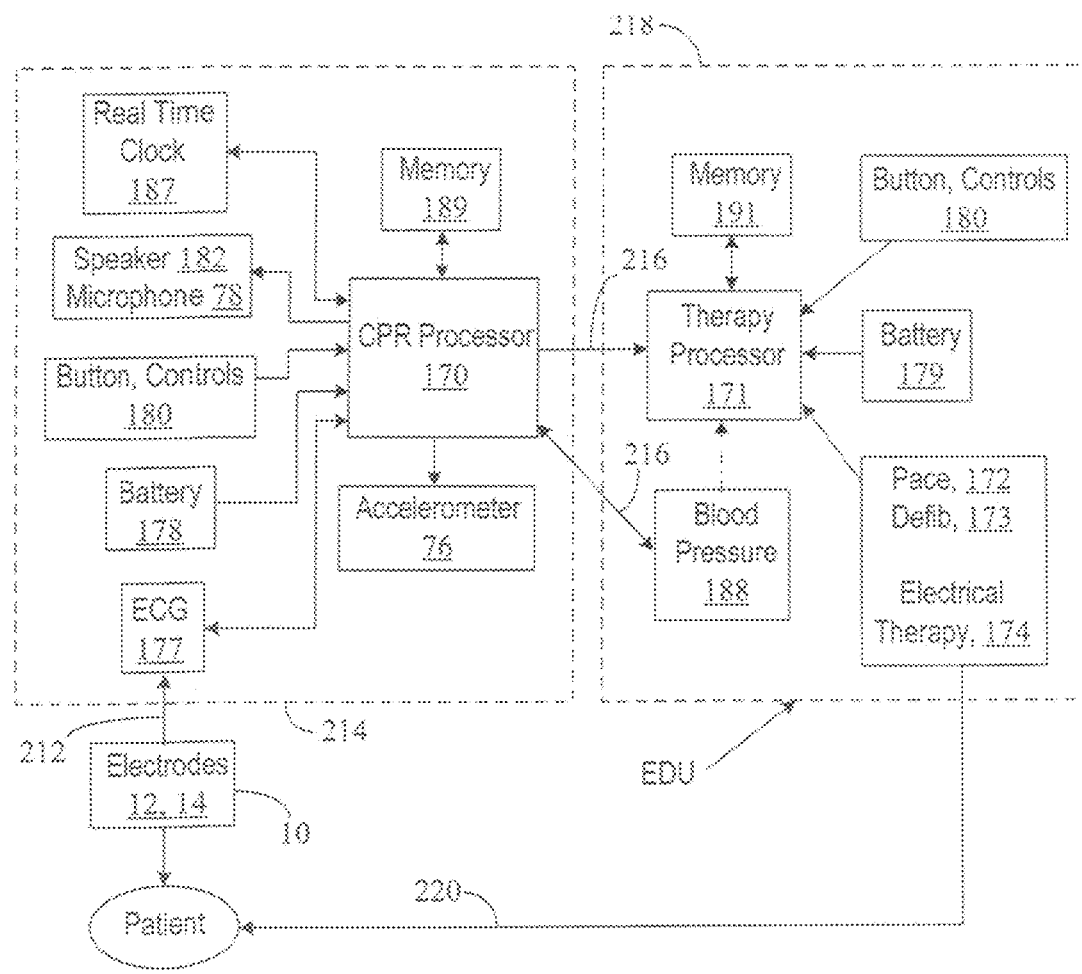
FIG. 10 is a block diagram of the electronic circuitry of an alternative implementation.

FIG. 8 shows the steps 140-146 for prompting the rescuer to assist the patient's breathing. After 12 breaths have been completed (step 144), the pulse oximetry or phonocardiogram system attempts to detect a pulse (step 145a), or, if the system does not include a pulse oximetry or phonocardiogram system, the resuscitation control box prompts the rescuer to check the patient's pulse. If no pulse is present, the resuscitation control box prompts the rescuer to press a Circulation Help button C (step 145b) that brings the rescuer back to the circulation portion of the flowchart. Otherwise, if a pulse is detected, then the flow chart of FIG. 8 returns to step 142.

The combined defibrillation and CPR resuscitation assembly provided can be less intimidating than conventional AEDs because the assembly is not devoted solely to defibrillation. Moreover, the resuscitation assembly is less intimidating because it accommodates common skill retention problems with respect to necessary techniques ancillary to defibrillation such as mouth-to-mouth resuscitation and CPR, including the appropriate rates of chest compression, the proper location for performing compressions, the proper manner of tilting the patient's head. In addition, because the rescuer knows that it may never even be necessary to apply a defibrillation shock during use of the resuscitation assembly, the rescuer may be more comfortable using the resuscitation assembly for mouth-to-mouth resuscitation and CPR. Unlike previous CPR prompting devices, the rescuer would be required to place the electrode assembly on top of the patient, but the rescuer would do this with the belief that the resuscitation assembly will be sensing the patient's condition and that the likelihood that the resuscitation assembly is actually going to apply a shock is low. If, during this resuscitation process, the resuscitation control box instructs the rescuer to press the "READY" button so that a defibrillation shock can be applied, the rescuer will likely feel comfortable allowing the shock to be applied to the patient. Basically, the resuscitation assembly simply tells the rescuer what to do, and by that point, given that the rescuer is already using the assembly, the rescuer is likely simply to do what the rescuer is told to do. Essentially, the rescuer will be likely to view the resuscitation assembly as simply being a sophisticated CPR prompting device with an additional feature incorporated into it, and since rescuers are less likely to be intimidated by CPR prompting devices than AEDs, they will be likely to use the resuscitation assembly when it is needed.

Figure 12A:
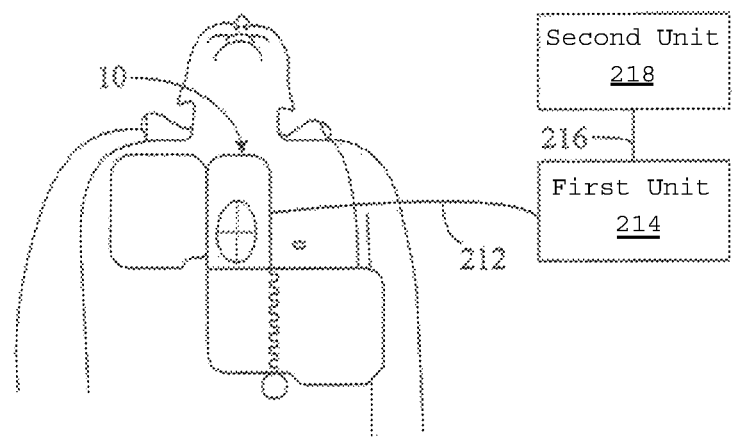
FIGS. 12A-12C are diagrammatic views of three possible implementations of first and second units.
Figure 12B:
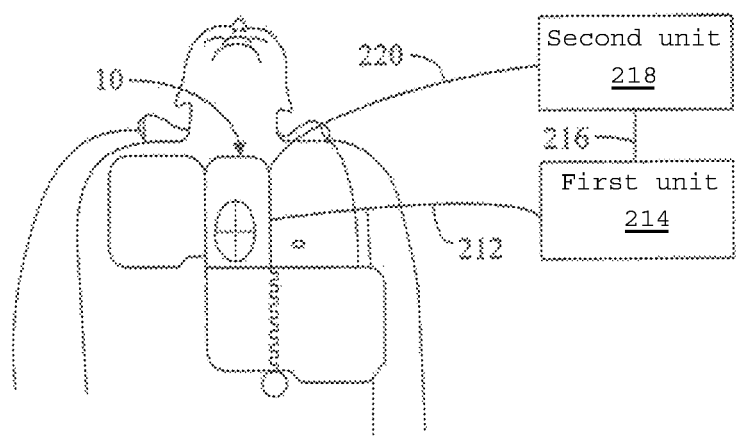
Figure 12C:
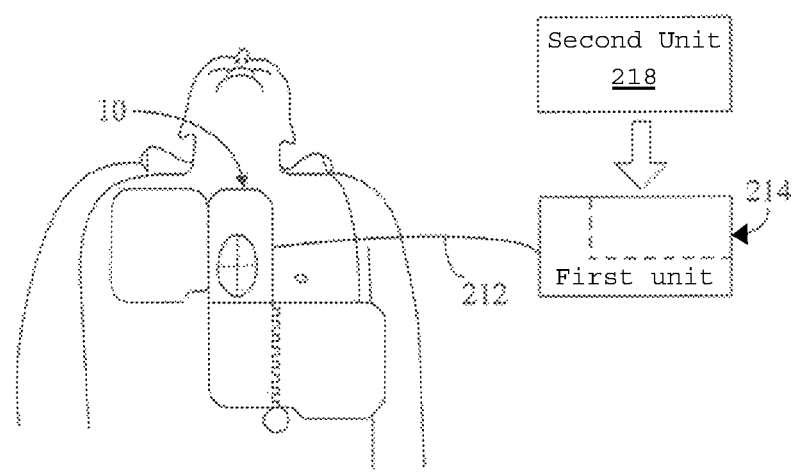

FIGS. 10, 11, and 12A-12C show alternative implementations in which an electrode pad assembly 10 is connected by a cable 212 to a first unit 214 containing the electronics for CPR prompting and resuscitation control. Another cable 216 connects the first unit to a second unit 218 containing the electronics for defibrillation and pacing therapy. A third cable 220 could be provided for making a direct connection from the second unit to the electrodes (FIG. 12B). The first unit 214 could be configured to receive the second unit 218 as an inserted module (FIG. 12C), in which case the electrical connection between the units are made internally without the use of cable 216. The primary function of the first unit 214 is to provide processing and control for CPR functions such as CPR prompts. The primary function of the second unit 218 is to provide processing and control of electrical therapy functions. The first unit includes a CPR processor 170, a battery 178, ECG circuitry 177 for amplifying and filtering the ECG signal obtained from the defibrillation pads 12, 14, a microphone 78 for recording the rescuer's voice as well as ambient sounds, an accelerometer 76, a real time clock 187, and a speaker 182 for delivering prompts to the rescuer. The second unit includes a therapy processor 171, a battery 179, buttons and controls 180, and memory 191.

The first unit could also be incorporated into the electrode pad assembly rather than being a separate box. The electronics could be provided on the rigid substrate 40 of the electrode pad assembly (FIG. 1).

Separate batteries 178, 179 and controls 180, 181 may be provided for the first (CPR) and second (therapy) units, thereby allowing the electronics in the first unit to provide CPR prompting to the operator without the need for the second unit. The cable 216 that connects the first and second units may be detachable. Memory 189 is provided in the first unit for storing information such as voice recording, ECG data, chest compression data, or electronic system status such as device failures that occur during daily self checks of the electronics initiated by a real time clock circuit.

The defibrillation electrode pad assembly 10 may incorporate defibrillation electrodes composed of a material that can be held against a patient's skin for extended periods of time (e.g., up to 30 days).

Figure 13A:
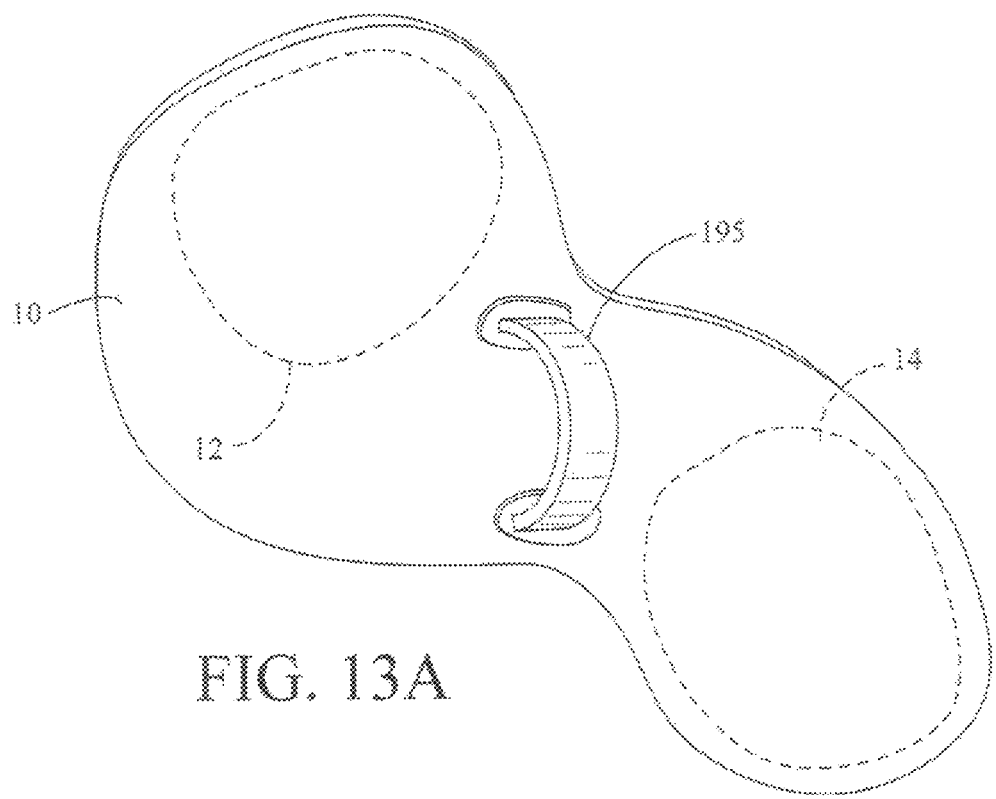
FIGS. 13A and 13B are drawings of two alternative implementations of the electrode pad assembly in which a handle is provided for the rescuer.
Figure 13B:
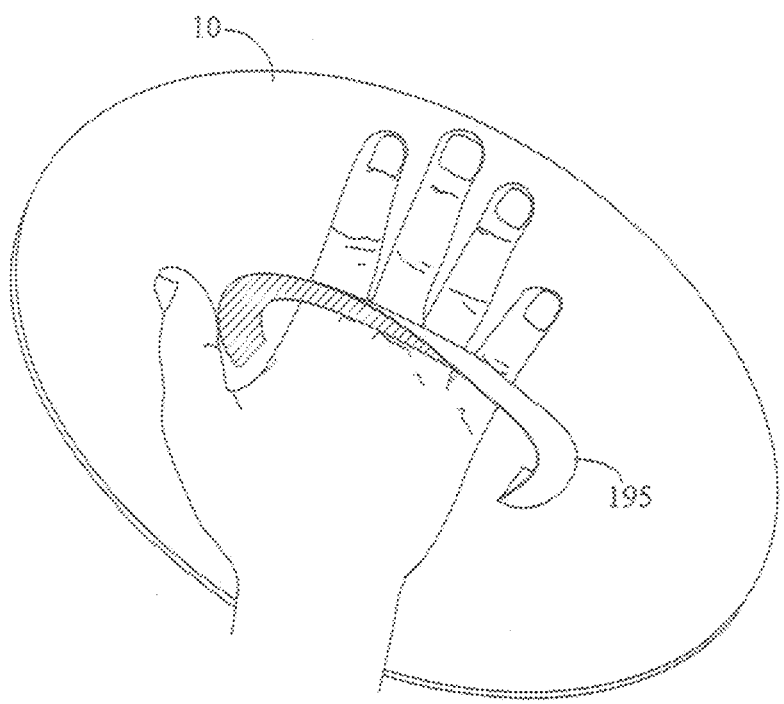

As shown in FIGS. 13A and 13B, the pad assembly 10 may also incorporate features on its upper surface facing the rescuer that provide a handle 195 for the rescuer during performance of CPR. The handle could take the form of a fabric loop (FIG. 13B) or a more rigid polymer member (FIG. 13A). The fabric could be sewn or adhered by adhesive or ultrasonic bonding to the pad 10 (FIG. 13B). The polymer handle could also be bonded by adhesive or ultrasonic bonding to the pad (FIG. 13A). It has been shown in studies that the maintenance of pressure on the chest during the decompression phase of chest compression results in a significant decrease in the effectiveness of the chest compressions. The handle 195 motivates the rescuer to pull up at least slightly during the decompression phase. The adhesive gel of the electrode pad, or other adhesive, can extend under the region where the rescuer's hands are placed during compression thus providing adhesion of the pad to the skin while the rescuer pulls on the handle during the decompression phase. Pulling up on the chest during the decompression phase has been shown to heighten negative intrathoracic pressure, increasing venous return and thus increasing blood flow during chest compressions.

In another implementation, the first unit may be adapted to be supported by the patient for long periods of time. The unit could be incorporated into the electrode pad assembly as suggested above, or it could be a separate unit configured to be worn by the patient. In such an implementation, the electronics of the first unit are designed to allow for long term monitoring of the patient's condition via the ECG 177 and physiological monitoring 176 circuitry. If a physiological condition is detected that is deemed hazardous to the patient by the CPR processor 170, based on analysis of the ECG and other physiological parameters, an alarm is sounded to the patient via the speaker 182.

An activity sensor and associated circuitry can inform the CPR processor of whether the patient is moving. For example, accelerometer 76 could serve as the activity sensor, and detect whether or not the patient is moving. Patient motion may be detected using a variety of different algorithms, including, for example the following: The acceleration signal is integrated over one-second intervals to provide an estimate of velocity. Velocity is integrated over the same one-second intervals to provide an estimate of displacement. The root means square velocity is calculated for each one-second interval. If either the RMS velocity exceeds 0.2 cm/s or the peak displacement exceeds 0.5 cm, the patient is determined to be moving.

If the algorithm determines that a cardiac emergency event is occurring, the first unit can send a message directly to a medical emergency response system, such as 911. This can be done using a variety of known communication techniques, e.g., Bluetooth, cellular phone, Ultra Wideband (UWB). If the activity sensor has determined that the patient is still moving during the cardiac emergency, the unit could also issue a prompt indicating, "Call 911 Immediately!"

The first unit will be able to determine the orientation of the patient, e.g., based on the accelerometer output. It can detect if a patient has fallen down and initiate a message to the emergency system. It can also determine whether the patient is lying on his back, the proper orientation for doing CPR. Thus, a specific prompt can be provided to the rescuer that tells them to roll the patient on their back prior to beginning CPR, should the device detect an improper orientation of the patient.

Other implementations may include signal analysis software for predicting the risk of a heart attack. When a threshold is exceeded in the value of that risk probability, a voice prompt may be provided to the patient via the speaker 182 to contact the medical emergency system. By using the motion detection capabilities of the accelerometer to measure and track a patient's activity level (PAL), and combining the activity level calculation with measurements of the ECG 177, e.g., ST-segment elevation (STE), the first unit is able to provide a predictor of the risk of an impending heart attack or cardiac arrest. An ST segment elevation exceeding a threshold such as 300 microvolts on the ECG provides an indicator of impending heart attack. In the preferred embodiment, ST segment elevation in the presence of increased physical activity is an indication of further risk of potential cardiac arrest. The calculation of risk probability may be accomplished by first performing a logistic regression of variables such as STE and PAL as predictors of cardiac arrest within 24 hours. The calculation may take the form of a linear regression equation such as 0.24 STE+0.12 PAL=RISK.

Alternatively, nonlinear regression may be performed to allow for a multiplicative term such as 0.24 STE+0.12 PAL+0.54 (STE*PAL)=RISK.

The multiplicative term heightens the importance of STE in the presence of PAL.

Parameters such as STE, PAL and RISK may additionally be stored in memory and multiple readings and calculations performed over time. The sequence of readings may then be analyzed for trends in the physiological state of the patient that can augment the RISK calculation taken at a single point in time. For instance, if STE is found to be steadily rising over a series of readings, the voice prompt may be triggered sooner than at a fixed threshold of 300 microvolts.

Additionally, the ECG may be analyzed to determine the interval between adjacent R-waves of the QRS complexes and using this interval to calculate heart rate variability as a running difference between adjacent R-R intervals. It is known that the R-R interval will vary following an ectopic beat or ventricular premature contraction (VPC). In a healthy heart, the R-R interval will decrease immediately following the VPC followed by a gradual return to steady state; a heart with an increased risk of heart attack will show a decreased level of variability. This effect is sometimes called heart rate turbulence. Two variables are calculated: (1) the Relative Change in R-R interval (RCRR) between pre- and post-VPB R-R intervals, RCRR=(R-R pre-VPB–R-R post-VPB)/R-R pre-VPB and (2) the slope of the change of R-R interval (SRR) while it is undergoing its post-VPB decrease. If the RCRR is non-negative and the slope SRR does not steeper than −2 ms/R-R interval then the patient is considered as at risk. Alternatively, the individual calculations may be included along with STE and PAL to create an integrated measurement vector as discussed in the preceding paragraphs. Other signal analysis algorithms may incorporate analysis of heart rate variability in the frequency domain, wavelet domain or using non-linear dynamics-based methods.

Since VPBs are often rare events, the defibrillation electrode pad 10 may include circuitry to stimulate the patient with a single pulse of low enough amplitude to cause a VPB without undue discomfort to the patient, under the patient's control. An additional control is provided on the low-profile button panel 20 so that the patient may initiate the pulse under their control. Alternatively, the device is programmed to automatically deliver the pulse at regular intervals such as at 24-hour intervals, at a time of day when the patient may conveniently have access to the device, such as in the morning. While the pulse generator 186 may be located in the second (therapy) unit, it is preferably contained as part of the first (CPR) unit.

In another implementation, the activity monitoring capability of the first unit may be utilized so that the activity state of the patient is continuously monitored. Using the activity monitoring capability and a real time clock 187, the first unit may detect when a patient has woken up in the morning. After there has been 10 minutes of regular motion detected, the unit may prompt the patient that it would like to perform a test. If the patient assents to the test indicated by a press of the TEST button on the low-profile button panel 20, the unit will send out a small current pulse, preferably a 40 millisecond pulse of 75 mA amplitude that is synchronized to the patient's ECG so that it occurs approximately 200 mS prior to the R-wave and after the T-wave so as not to introduce any arrhythmias. The pulse will safely cause a VPB in the patient which can then be used to measure the autonomic response to a VPB to provide regular calculations of the autonomic response to a VPB as measured by such parameters, though not limited to, STE and PAL, and providing a daily update to the RISK calculation.

Additional physiological measurement, preferably that of blood pressure, may be incorporated into the RISK calculation. A sudden change in systolic or mean arterial blood pressure of greater than 10-15 points is indicative of an increased risk of cardiac arrest. In the preferred embodiment, the blood pressure measurement device would be a handheld, inflated cuff blood pressure device 188. The blood pressure cuff 188 would have wireless communication capability with the CPR Processor 170 and at the conclusion of each measurement, the blood pressure reading along with a date and time stamp would be stored in memory 189 of the CPR Processor 170 for subsequent use in calculating RISK. This scheme would allow the patient to carry the small blood pressure cuff along with them during their daily activities and take blood pressure measurements at regular intervals without having to return home. Alternatively, the blood pressure measurement device may communicate with the therapy processor and may additionally get power from and be physically connected to the second (therapy) unit by a cable. The patient will then be required to take regular blood pressure readings at the second unit, typically a larger device that may or may not be portable. Communication of the blood pressure readings may be accomplished over a cable between the first (CPR) and second units (therapy) units, e.g., cable 216, or wirelessly, using such technology as Bluetooth.

The second unit 218 may in some implementations be thought of as an energy delivery unit (EDU), in which case it would incorporate a defibrillator 172, pacer 173, or other electrical therapy 174. In some implementations, the EDU would be small and light enough to be worn in a harness or belt to be carried around continuously by the patient. The EDU 218 may in some cases not contain a therapy processor 171, but be a "dumb" device that requires the controls provided by connection to the processor in the first (CPR) unit, e.g., on the defibrillator pad 10, in order to deliver electrical therapy to the patient.

In some cases, the patient may not even own an EDU due to the significant costs inherent in the high-voltage components necessary. The patient would only own the first unit and defibrillator pad, as the components incorporated in them are less expensive, e.g., they can be manufactured from less-expensive, consumer-type electronics. In such a case, when the patient did not own the EDU, and had a heart attack, a bystander or family member who encountered the cardiac arrest victim would be prompted to begin CPR. It has been shown now in several studies that performing good CPR for extended periods prior to delivery of a shock is not detrimental to long term survival, and can in some cases increase survival rates. CPR would thus begin with built-in prompting and when the paramedic arrives with the defibrillator it can be connected to the pads to deliver the electrical therapy. If the first (CPR) unit is separate from the electrode pad assembly, the EDU connection to the electrodes could be direct, or via a cable connected to the first (CPR) unit. If the defibrillator is an EDU or other compatible device, patient and performance data stored by the first (CPR) unit may be downloaded to the defibrillator.

Many other implementations of the invention other than those described above are within the invention, which is defined by the following claims. For example, the defibrillation pads 10, 12 may be separable from the CPR-prompting first unit and be connected at the time that the EDU is brought to the scene; the defibrillation pads may be connected both electrically and mechanically to the CPR-prompting first unit at that time. A greater amount of the control functionality may be put into the first unit, leaving essentially only the circuitry for providing the defibrillation pulses in the second unit. The first unit may be incorporated into the defibrillation electrode pad assembly, or made a separate unit connected to the pad assembly by one or more cables. The second unit may connect to the first unit by one or more cables, or by a wireless connection. The defibrillation pulses may pass through the first unit (FIG. 12A), or be routed directly to the defibrillation electrodes via one or more cables running from the second unit to the electrodes (FIG. 12B). The second unit may connect to the first unit by being plugged into the first unit (FIG. 12C), without the need for a cable (e.g., the second unit could be a defibrillation module that plugs into the first unit).

In some implementations the second (therapy) unit can provide pacing therapy as well as defibrillation therapy. Pulse detection methods other than pulse oximetry and phonocardiogram may be employed. Any method capable of detecting a victim's pulse can be used for pulse detection.

Figure 14:
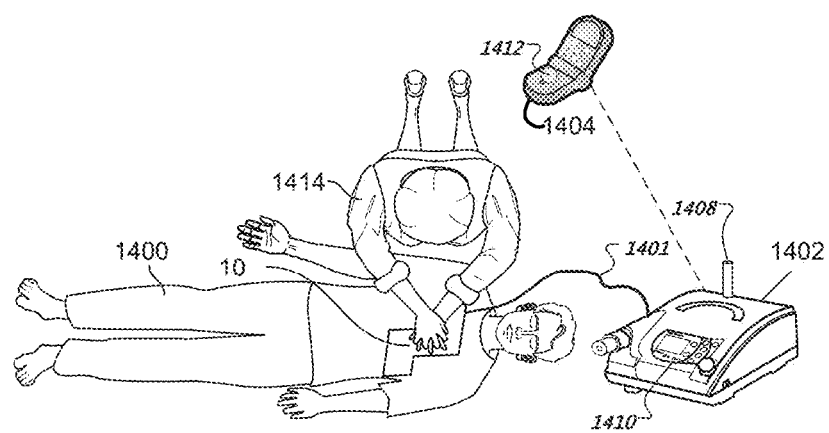
FIG. 14 is a diagram of a treatment unit and a control unit.

Referring to FIG. 14, in some embodiments, the electrode pad assembly 10 can be connected by a cable 1401 to a treatment unit 1402 containing electronics for delivering treatment to a patient 1400, such as electronics for defibrillation and pacing therapy. For instance, the treatment unit 1402 can be a defibrillator, such as an AED. The operation of the treatment unit 1402 can be controlled by a control unit 1404, such as a mobile device. In the example of FIG. 14, the treatment unit 1402 is in wireless communication with the control unit 1404, e.g., through a short-range wireless protocol such as Bluetooth® communication or another type of wireless communication. In some examples, the treatment unit 1402 can be in wired communication with the control unit 1404, e.g., through a cable connection.

The treatment unit 1402 can act as a power source and can include electronic components, such as a battery, a capacitor, and other electronic components that enable the treatment unit 1402 to provide treatment to the patient 1400. The treatment unit 1402 can also include a communication module 1408, e.g., an antenna, for communicating wirelessly with the control unit 1404. In some examples, the treatment unit 1402 can include basic controls 1410, such as a power switch and a shock/analyze controller, that can be used by a rescuer 1414 to operate the treatment unit 1402 without the control unit 1404.

The control unit 1404 can be a mobile computing device, such as a mobile phone (e.g., an iPhone®), a tablet (e.g., an iPad®), a wearable computing device such as a smart watch or glasses (e.g., a Glass® wearable computing device), or another type of mobile computing device. The control unit 1404 executes a software application 1412 (referred to herein as an "app") that controls the operation of the treatment unit 1402, provides information and instructions to a user 1414 of the control unit 1404 (e.g., a rescuer), and receives input from the user 1414. In some examples, the app can be a generalized app that enables the control unit 1404 to control various types of treatment units 1402, such as treatment units 1402 produced by various manufacturers. In some examples, the app can be specific to one or more particular brands or models.

The app 1412 can receive status information about the patient from the electrode pad assembly 10. In some examples, the control unit 1404 can receive the status information directly from the electrode pad assembly 10, e.g., through a wired or wireless connection with the electrode pad assembly 10. In some examples, the control unit 1404 can receive the status information from the treatment unit 1402, which receives the status information from the electrode pad assembly 10.

The app 1412 analyzes the status information to determine the condition of the patient 1400. For instance, the app 1412 can determine if the patient's rhythm is shockable. If the rhythm is shockable, the app 1412 can command the treatment unit 1402 to deliver a shock to the patient 1400, e.g., automatically or upon approval by the user 1414. In some cases, the app 1412 can determine the appropriate energy and duration for the shock and the appropriate number of shocks. If the rhythm is not shockable, the app 1412 can instruct the user 1414 to deliver CPR to the patient 1400. In some examples, the app 1412 can command the treatment unit 1402 to analyze the status information and to deliver a shock to the patient 1400 if appropriate, e.g., automatically or upon approval by the user.

The app 1412 communicates information and instructions to the user 1414, e.g., through visual, audio, or tactile communications. The app 1412 can display information and instructions as images and/or text on a display interface of the control unit 1404. In one example, the app 1412 displays step-by-step instructions and simple figures to guide the user in delivering CPR to the patient. The app 1412 can provide audio information through speakers of the control unit 1404. In one example, the app 1412 speaks "Clear: Shocking Patient" prior to commanding the treatment unit 1402 to apply a shock. In one example, the app 1412 sounds a rhythmic tone (e.g., a beep) to assist the user in delivering compressions at the proper rate. The app 1412 can provide tactile information through a vibration component of the control unit 1404. For instance, the app 1412 can cause the mobile device 1404 and/or a unit on the electrode pad assembly 10 to vibrate when a new instruction is displayed on the display interface. Other ways of communicating with the user can also be used.

The app 1412 can also receive input from the user 1414. For instance, the user can tap the screen with his finger or a pointing device, such as a stylus, to input information to the app 1412. In one example, the user can tap an "Approve" button to approve the delivery of a shock to the patient 1400. Information can also be received by other methods. For instance, the user can input information, such as information about the patient, to the app through a keyboard or keypad of the control unit 1404. The user can speak into a microphone and the app 1412 can use voice recognition technology to recognize voice commands. For instance, the user can ask for more information or give a command to the app 1412, such as commanding the app 1412 to dial 9-1-1 to report an emergency. In some examples, the user's speech can be processed by a speech recognition program. Other forms of input can also be used.

In some examples, the app 1412 can operate in either a rescue mode or a training mode. In rescue mode, the control unit 1404 communicates with the treatment unit 1402 to provide treatment to a real patient 1400. In training mode, the user-facing operation of the app 1412 is similar to the rescue mode operation of the app, but the control unit 1404 does not communicate with the treatment unit. That is, the app 1412 acts as a simulator that allows the user 1414 to interact with the control unit 1404 as if he were in a real rescue situation. In some examples, the training mode can include a simulation component, which simulates the operation of the app 1412 in a real rescue situation; and a teaching component, which provides recorded instructions, demonstrations, videos, quizzes, or other approaches to teaching the user about the app 1412 or about rescue techniques in general.

The app 1412 can offer multiple levels of operation to the user 1414. Each successive level can be targeted at users with greater experience. Thus, each successive level can provide access to a wider range of capabilities of the app. In addition, the prompts and instructions that the app 1412 provides to the user can depend on the level. For instance, in a basic mode directed to inexperienced users, only basic functions of the app 1412 can be accessed, and detailed instructions for how to proceed in a rescue situation can be provided. In an advanced mode directed to experienced professional users, a more complete set of functions of the app 1412 can be accessed, and fewer instructions are provided so as not to distract the user. In some examples, training mode can provide a teaching component associated with each level that is designed to teach the user about the capabilities of the app 1412 at that level and associated rescue techniques.

In some examples, the app 1412 can access a stored indicator of the user's proficiency on startup, and can run the appropriate level based on the stored indicator. The indicator can be stored locally on the control unit 1404 or in a remote data storage accessible through a communications network, such as the Internet. In some cases, the indicator can be reflective of the user's history of using the app 1412, e.g., in rescue mode, training mode, or both. For instance, the indicator can reflect the level that the user has reached in training mode. In some cases, the indicator can be specified by the user or by a third party, such as the user's supervisor. In some examples, no indicator is stored and the app 1412 can prompt the user to enter his proficiency on startup.

Figure 15:
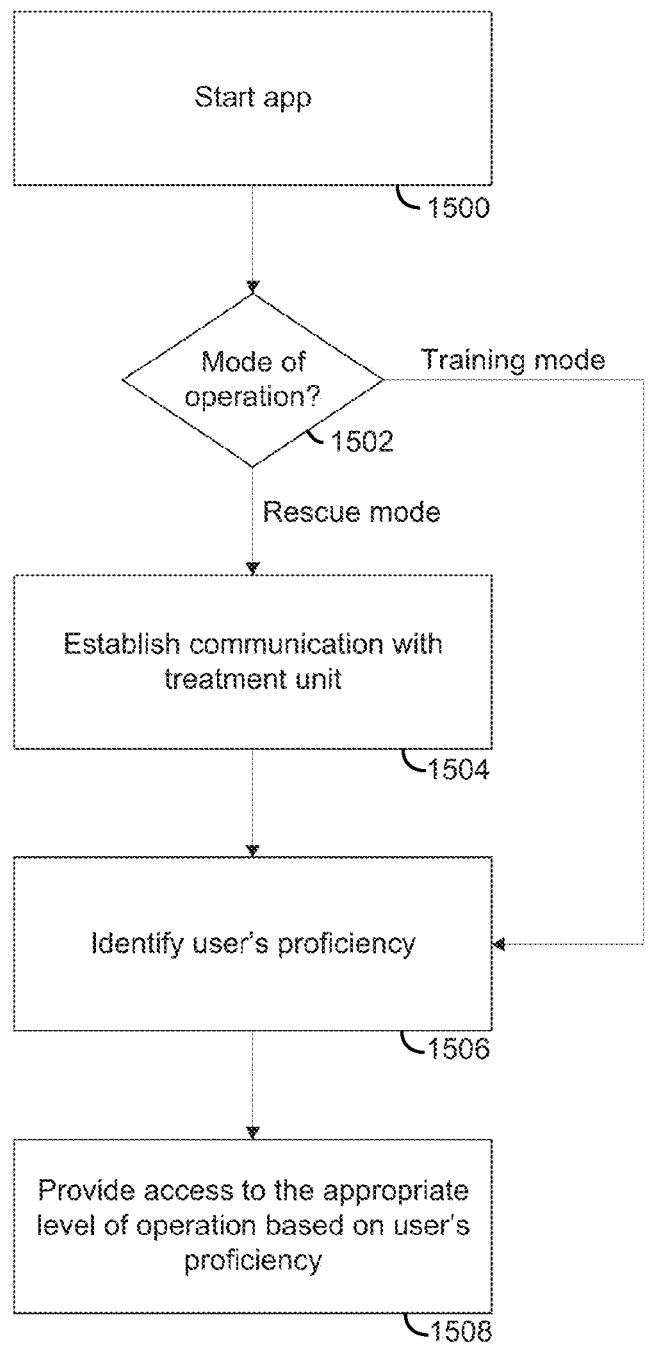
FIG. 15 is a flowchart.

Referring to FIG. 15, in operation, when the app is started up (1500), the app determines whether to run in rescue mode or training mode (1502). In some examples, the app can prompt the user to identify the mode, e.g., by a voice command or by tapping a button on the display interface. For instance, if the user does not answer the prompt within a set period of time (e.g., ten seconds, thirty seconds, one minute, or another period of time), the app can run in rescue mode by default. In some examples, the app automatically run in rescue mode if it detects the presence of a treatment unit, such as an AED.

If the app runs in rescue mode, the app causes the control unit to establish wireless communication with the treatment unit (1504). In some examples, if the app detects the presence of a treatment unit, a wireless connection can be automatically established. In some examples, the app requests user input, such as user approval to establish the connection or user input to identify the treatment unit.

In both training mode and rescue mode, the user's proficiency is identified by the app (1506). In some examples, the app can retrieve the indicator of the user's proficiency from local data storage on the control unit or from an Internet-accessible remote data storage. In some examples, the app can prompt the user to enter an indicator of his proficiency.

Based on the user's proficiency, the app provides access to the appropriate level of operation (1508). Depending on the level of operation, the user can have access to various capabilities of the app, and instructions and information can be provided to the user as appropriate.

Figure 16:
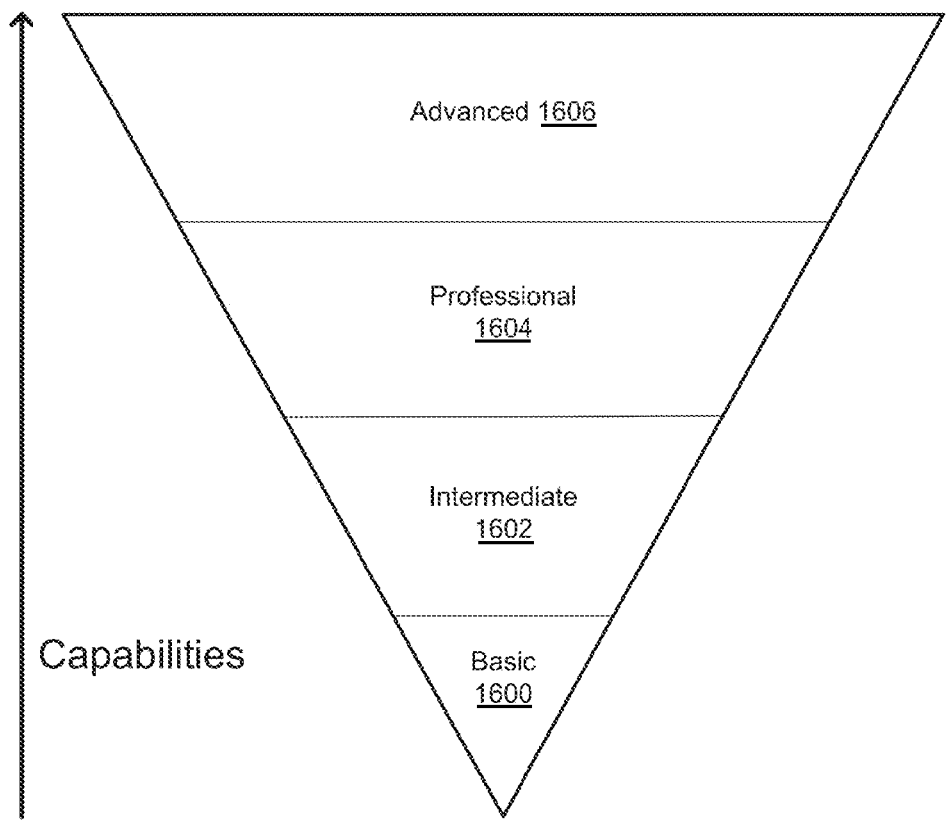
FIG. 16 is a chart of example levels of operation of a control unit app.

Referring to FIG. 16, in one example, the app can provide four levels of operation: a basic level 1600, an intermediate level 1602, a professional level 1604 and an advanced level 1606. Each level provides access to some or all of the capabilities of the level(s) below it and additional capabilities for that particular level. In some examples, more or fewer levels can be provided. In training mode, the teaching component for each level can provide a curriculum that is designed to teach the user how to perform rescue techniques in coordination with the operation of the app at that level, while the simulation component allows the user to practice the operation of the app at that level.

In the example of FIG. 16, the basic level 1600 is designed for lay users who have basic knowledge of compressions but little experience (e.g., users who have completed a basic CPR training course). At the basic level, the app primarily acts as a prompting tool that provides the user with detailed instructions for how to proceed in a rescue situation. For instance, the app can provide a sequence of instructions, questions, and information to the user as text on the screen, audio, or both. The basic level can offer automated 9-1-1 calling capability, rhythm capabilities for CPR, and feedback about compressions.

Figure 17:
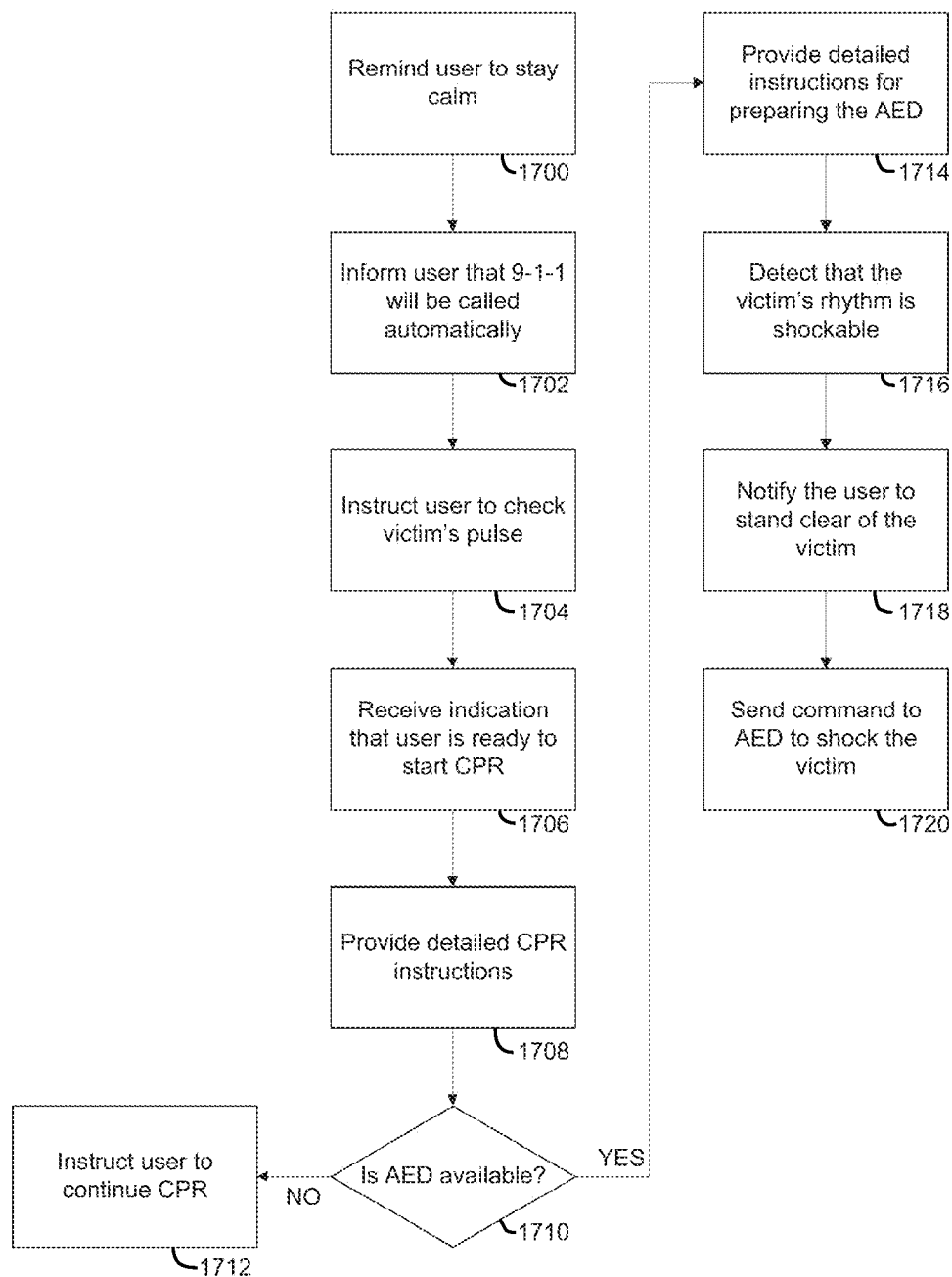
FIGS. 17-19 are flowcharts.

Referring to FIG. 17, in one example set of instructions for the basic level 1600, the user is reminded to stay calm (1700) and informed that 9-1-1 will be called automatically (1702). The user is instructed to check the victim's pulse (1704) and asked to indicate when he is ready to start CPR (1706), e.g., by tapping on the display interface or by speaking a command. When the user responds that he is ready, the app 1412 provides detailed, step-by-step CPR instructions (1708), including providing a rhythm for compressions. In some examples, the control unit 1404 can act as a feedback device to provide feedback about the compression speed, depth, or both, as described in U.S. patent application Ser. No. 13/788,720, the contents of which are incorporated herein by reference.

At an appropriate point during CPR, the user is asked if an AED is available (1710). If not, the user is instructed to continue CPR as directed (1712). If an AED is available, the user is provided with detailed instructions for preparing the AED (1714), including turning on the AED, opening the electrode pad package, and applying the electrode pad assembly to the victim.

Once the AED is prepared, the app analyzes the condition of the victim to determine if the victim's rhythm is shockable. When the app determines that the victim's rhythm is shockable (1716), the user is notified to stand clear of the victim (1718) and the app automatically sends a command to the AED to deliver a shock to the victim (1720), e.g., after receiving confirmation that the user is clear of the victim. That is, in this example, the basic level does not provide the user access to the AED controls within the app.

In some examples, the app can command the AED to analyze the condition of the victim to determine if the victim's rhythm is shockable. When the AED determines that the victim's rhythm is shockable, the AED communicates with the app, which notifies the user to stand clear of the victim. The app can then instruct the AED to deliver a shock to the victim, e.g., after receiving confirmation that the user is clear of the victim.

Other information and instructions can also be provided at the basic level. For instance, the app can remind the user about personal safety issues, such as wearing gloves or a face mask. The app can ask the user if there is another person available to help, and can provide instructions to that other person.

Referring again to FIG. 16, the intermediate level 1602 is designed for users who have proficient knowledge of CPR and AEDs, e.g., users who have completed AED training. At the intermediate level 1602, the capabilities offered by the app are substantially the same as the capabilities offered at the basic level, but fewer questions and instructions are presented to the user so as not to distract the user.

Figure 18:
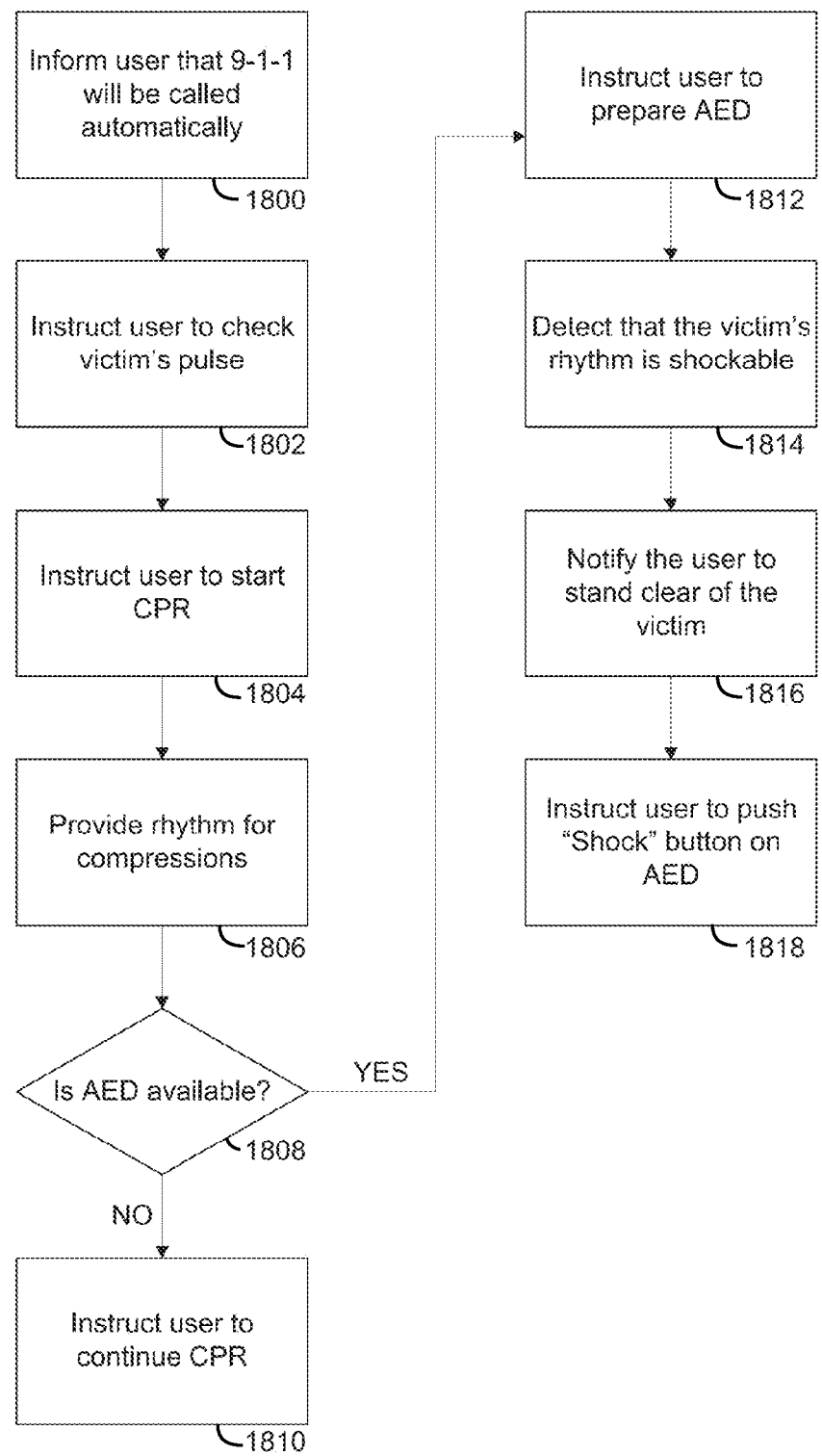

Referring to FIG. 18, in one example set of instructions for the intermediate level, the user is informed that 9-1-1 will be called automatically (1800). The user is instructed to check the victim's pulse (1802) and instructed to start CPR (1804). The app can provide a rhythm for compressions (1806) during CPR. In some examples, the control unit can act as a feedback device to provide feedback about the compression speed, depth, or both, as described in U.S. patent application Ser. No. 13/788,720, the contents of which are incorporated herein by reference.

At an appropriate point during CPR, the user is asked if an AED is available (1808). If not, the user is instructed to continue CPR as directed (1810). If an AED is available, the user is instructed to prepare the AED (1812).

Once the AED is prepared, the app analyzes the condition of the victim to determine if the victim's rhythm is shockable. When the app determines that the victim's rhythm is shockable (1814), the user is notified to stand clear of the victim (1816) and instructed to press the "Shock" button on the AED (1818) when clear of the victim. That is, in this example, the intermediate level does not provide the user access to the AED controls within the app.

In some examples, the intermediate level does not provide the user access to the AED controls within the app; the user is limited to using the controls on the AED itself. When the app detects that a shock should be delivered to the victim, the app notifies the user to stand clear of the victim (1814) and asks the user to press the "Shock" button on the AED (1816) when clear of the victim.

Other information, instructions, and capabilities can also be provided at the intermediate level. For instance, the app can respond to a user request for help by providing additional instructions about a particular technique (e.g., by providing step-by-step instructions for the preparation of the AED).

Referring again to FIG. 16, the professional level 1604 is designed for professionals, such as first responders, who have substantial training in CPR, AEDs, and general rescue techniques. For instance, police officers and fire fighters may generally operate the app at the professional level. At the professional level, the app provides few instructions to the user. For instance, the app can provide an instruction to the user only as a reminder, e.g., if the app detects that the user has forgotten a step or if a particular step is a commonly overlooked step. The professional level app can offer AED control capabilities, such as a shock/analyze capability performed by the app itself and operable by the user. The professional level app can also respond to instructions from the user. For instance, the user can speak instructions asking the app to communicate with a dispatcher to send a paramedic team to treat a potential heart attack. In addition, the professional level provides access to all of the capabilities available at the basic and intermediate levels. Other information, instructions, and capabilities can also be provided at the professional level.

Figure 19:
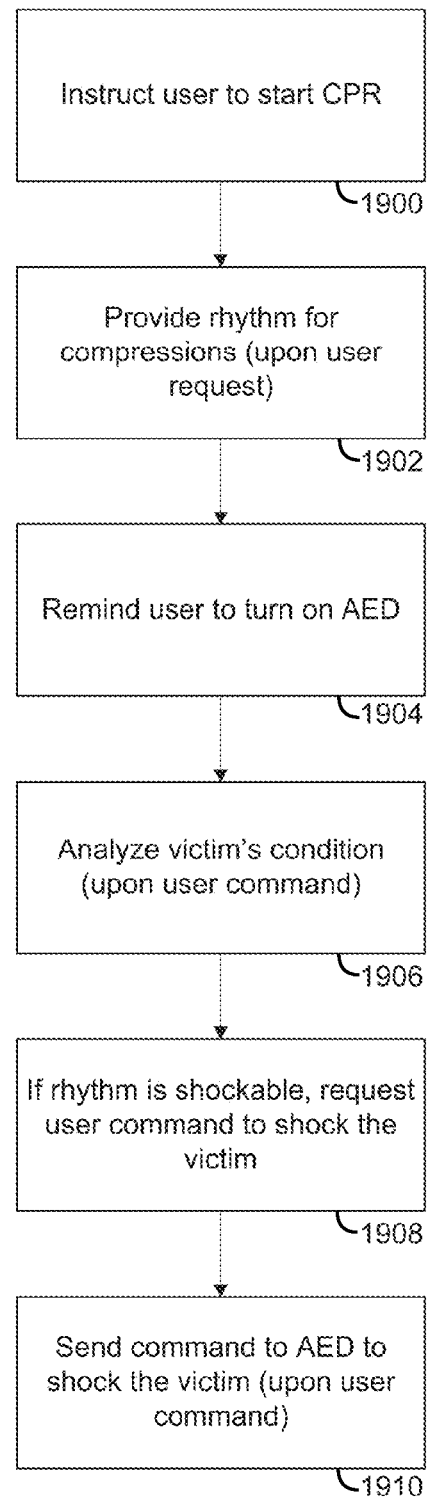

Referring to FIG. 19, in one example operation of the app at the professional level, the user is instructed to start CPR (1900). The app can provide a rhythm for compressions (1902) during CPR. In some examples, the control unit can act as a feedback device to provide feedback about the compression speed, depth, or both, as described in U.S. patent application Ser. No. 13/788,720, the contents of which are incorporated herein by reference. In some examples, the app can provide a rhythm and/or feedback only if requested by the user.

If the user does not turn on the AED, the user can be provided with a prompt to turn on the AED through the app (1904), e.g., by clicking or tapping on a button on the display interface or by speaking a command. The app presents a shock/analyze capability to the user, e.g., as buttons on the display interface or as commands that can be spoken. When the app receives the user's command to analyze, the app analyzes the victim's condition (1906). If the app determines that the victim's rhythm is shockable, the app asks for the user's command to shock the victim (1908), e.g., by presenting a visual, audio, or vibration indicator that the rhythm is shockable. Upon receiving the user's command to shock (e.g., a tap on a button on the display interface or a spoken command), the app sends a command to the AED to deliver a shock to the victim (1910). That is, in this example, the professional level provides the user with access to AED controls within the app.

Referring again to FIG. 16, the advanced level 1606 is targeted for advanced users, such as paramedics or emergency medical technicians (EMTs), who have had substantial training and experience in emergency situations, such as advanced life support training. The advanced level provides access to all of the capabilities available at the professional level, and likewise provides few instructions to the user.

In addition, the advanced level can allow the user to connect one or more monitors to the control unit to gain a more detailed and accurate overview of the victim's condition. For instance, the user can connect a multiple lead ECG to the control unit, such as a three-lead ECG, a twelve-lead ECG, an eighteen-lead ECG, or another type of ECG. Plots corresponding to each of the leads of the ECG can be displayed on the display interface. In some examples, plots corresponding to all of the leads can be displayed simultaneously and the user can scroll through the plots. In some examples, the user can request a plot, e.g., by a voice command (e.g., speaking the name of the lead) or by selecting the plot from a list of available plots.

Other information, instructions, and capabilities can also be provided at the advanced level. For instance, the advanced level can provide recording and charting capabilities, e.g., a data recorder that records ECG traces or a voice recorder that records a paramedic's ongoing voice narration of an emergency rescue situation.

Figure 20:
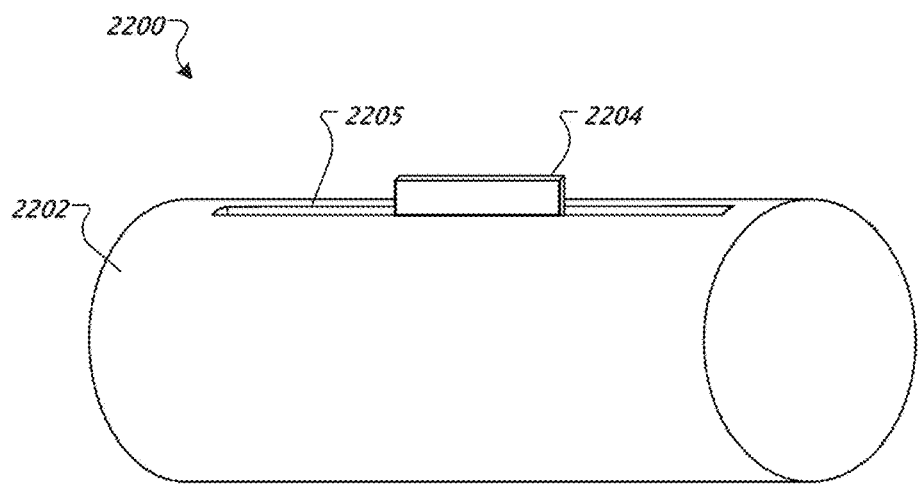
FIGS. 20-23 are diagrams of a portable multiple lead ECG package.
Figure 21A:
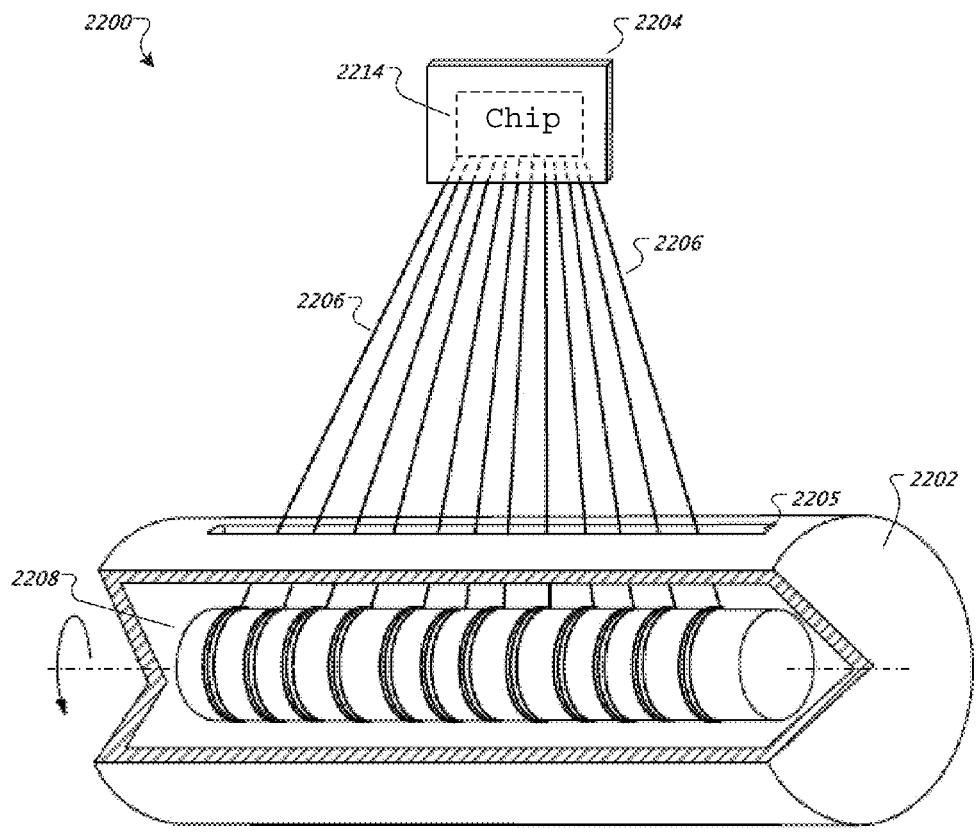
Figure 21B:
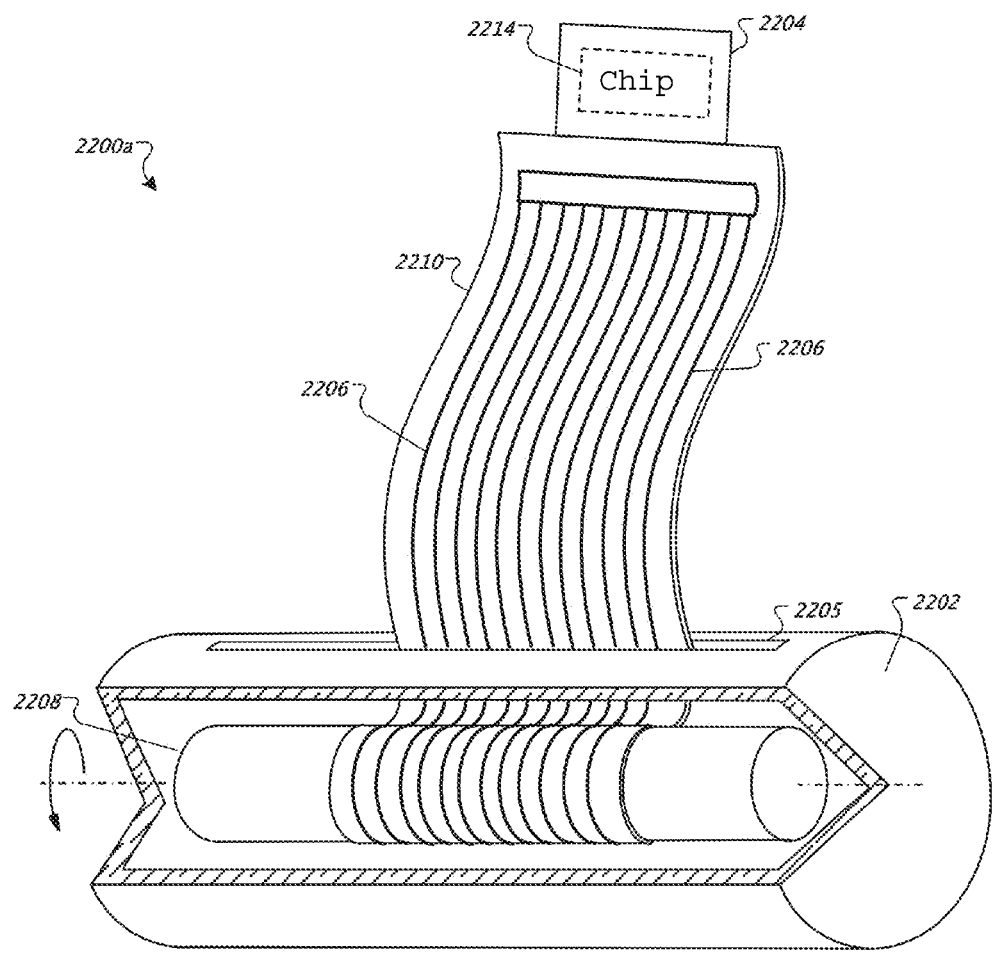
Figure 22:
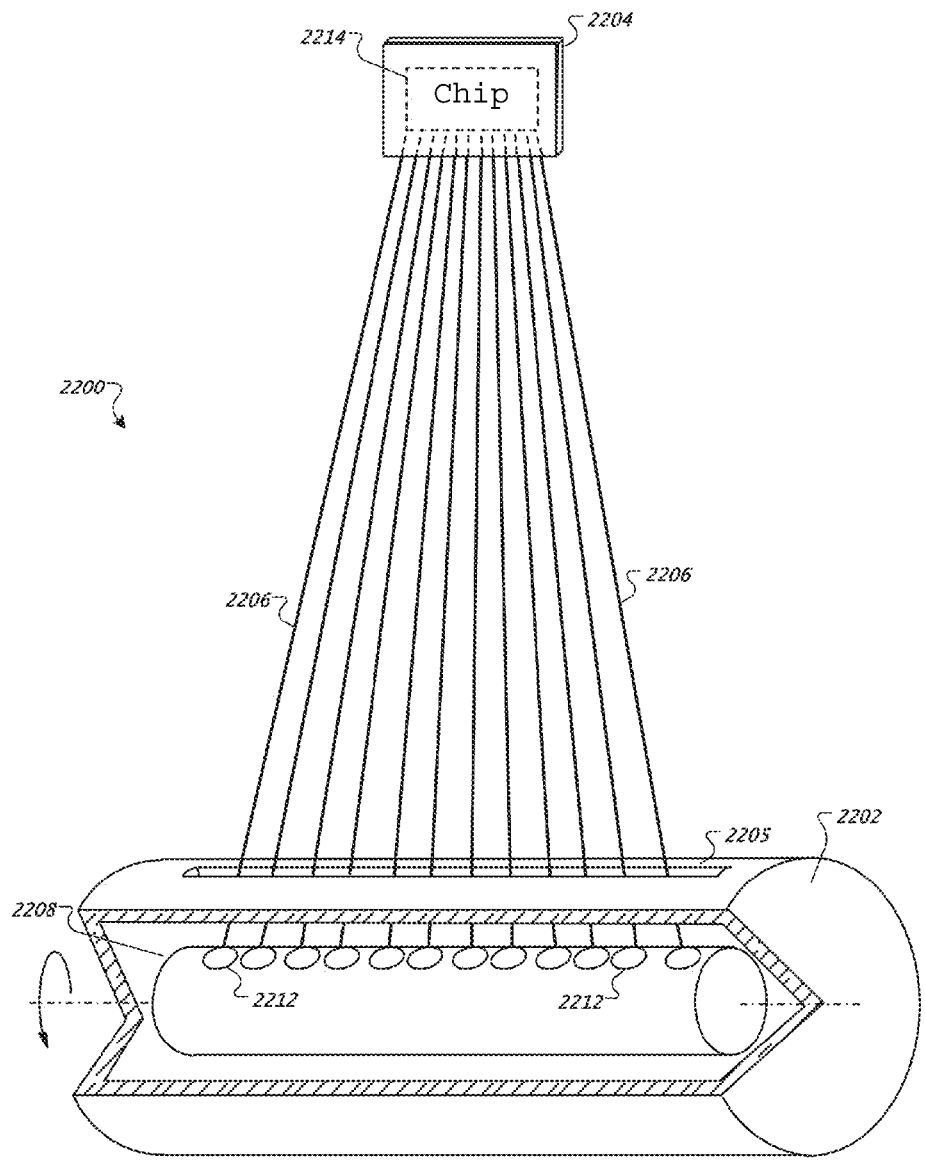

Referring to FIGS. 20-22, in some examples, a portable multiple lead ECG package 2200 can be easily carried by a rescuer, e.g., in a backpack or supply pack. In the example of FIGS. 20-22, the ECG package 2200 is for a 12-lead ECG, but other types of ECGs are also possible. The ECG leads in the ECG package 2200 can be attached to the control unit 1404, e.g., to an input port of a mobile device. The portable ECG package 2200 can be carried around by medical personnel, enabling those medical personnel to have easy access to complex ECG equipment, without the danger of damaging the ECG electrodes or tangling the ECG cables.

Referring to FIG. 20, a cylindrical housing 2202 is formed of a rigid, durable material, such as a hard plastic. A pull tab 2204 is accessible at a slit 2205 in the housing. For instance, the pull tab 2204 can protrude through the slit 2205. In some examples, the pull tab 2204 is a plug configured to plug into a port of the control unit (e.g., a mobile device, such as a mobile phone or tablet). For instance, the pull tab 2204 can be a mini-USB connector. In some examples, the pull tab includes a cover (not shown) that protects the mini-USB connector. The housing 2202 can be of a size that is easily carried, e.g., within a backpack or purse. For instance, the housing 2202 can have a diameter of less than about 2 inches, e.g., less than about 1 inch. The housing 2202 can have a length of less than about 5 inches, e.g., less than about 3 inches.

In some examples, the ECG package 2200 is provided enclosed in a wrapper, e.g., to protect the integrity and cleanliness of electrode pads therein. For instance, the ECG package 2200 can be packaged in a wrapper that provides a high moisture vapor barrier, such as a high moisture vapor transmission rate (MVTR) material, e.g., a polyfoil substrate. In some examples, the housing itself 2202 is formed of a material that provides a high moisture vapor barrier. In some examples, the slit 2205 can be closed by a gasket material that allows the pull tab 2204 to be accessed but prevents moisture from entering the interior of the housing.

FIGS. 21A and 21B show cutaway views of the ECG package 2200 and an alternative example of an ECG package 2200a. ECG cables 2206 are wrapped around one or more dispensers 2208. For instance, in the examples of FIGS. 21A and 21B, the cables are wrapped around a core 2208 that is oriented along the length of the housing 2202. In some examples, the core 2208 can be a roller that is fixed to the housing, e.g., by holders that allow the core to rotate relative to the housing. In some examples, the core 2208 can be loose within the housing. A distal end of each ECG cable 2206 is connected to the pull tab 2204. The ECG cables 2206 can have a length sufficient to connect the pull tab 2204 to the control unit and to connect electrodes on the proximal end of the ECG cables 2206 to the victim. For instance, the ECG cables 2206 can have a length of about 36 inches, about 30 inches, about 24 inches, or another length.

A chip 2214, such as a memory chip or a processor, located in or near the pull tab 2204 can store and/or process ECG data carried by the ECG cables 2206. For instance, the ECG signals transmitted through the ECG cables 2206 can be stored on the chip 2214 so that the signals can later be read and analyzed by a physician at a hospital. By storing the signals on the chip 2214, the stored data can be easily transported to the hospital.

When a rescuer pulls the pull tab, the ECG cables 2206 unwind from their wrapped configuration around the core 2208 and can be pulled out of the housing 2202. For instance, the core 2208 can spin as the pull tab 2204 is pulled, thus releasing the ECG cables 2206. By storing the ECG cables 2206 in this wrapped configuration, the chance of the cables tangling or breaking during transportation and/or unwinding can be minimized.

In some examples (e.g., FIG. 21A), each ECG cable 2206 is independent of the other ECG cables, and the ECG cables 2206 join together at the pull tab 2204. For instance, each ECG cable 2206 can be wound around a separate section of the core 2208. In some cases, the core 2208 can be beveled at the winding position of each ECG cable 2206 to help keep the cables in place. In some examples (e.g., FIG. 21B), some or all of the ECG cables 2206 are aggregated into a multi-cable ribbon 2210. The ribbon 2210 containing the ECG cables is wound around the core 2208 as a single unit and can be unwound from the core as a single unit. Once the ribbon 2210 is completely unwound, the individual ECG cables 2206 can be pulled apart.

In some examples, each ECG cable 2206 can be wound individually around a corresponding core that can rotate relative to the housing, such as a radially oriented core. Other configurations of ECG cables 2206 within the housing are also possible. For instance, each ECG cable 2206 can be contained within a package, such as a pouch, within the housing.

Referring to FIG. 22, each ECG cable 2206 has an electrode pad 2212 at its proximal end. That is, when the ECG cables 2206 are wound around the core 2208, the electrode pad 2212 is also wound around the core 2208. Once the length of the electrodes has been pulled out of the housing, the electrode pads 2212 are accessible and can be placed on the victim as appropriate. For instance, each electrode pad 2212 can include a conductive gel embedded within a self-adhesive pad that is connected to the corresponding ECG cable 2206.

In some examples, the electrode pads 2212 are disposed directly on the core 2208, which can be coated with a release liner, such as silicone, to enable the pads 2212 to be removed quickly and easily and with little to no damage to the pads. In some examples, the electrode pads 2212 can be protected by a release liner coating, such as silicone, which can be removed by the rescuer after removing the pads 2212 from the core 2208 and prior to placing the pads on the victim. In some examples, the electrode pads 2212 are encased in a packaging, and the packaged electrode pads 2212 are wound around the core 2208. For instance, the packaging can be an envelope that provides a high moisture vapor transmission rate barrier, such as a polyfoil substrate.

In some examples, the ECG cables 2206 can be different lengths. For instance, in some cases, each individual ECG cable 2206 can be a unique length, such that as the ECG cables 2206 are unwound from the core 2208, each ECG cable 2206 can be pulled off of the core 2208 separately from each other ECG cable 2206. In some cases, two or more groups of ECG cables 2206 can be formed, the ECG cables 2206 in each group having a unique length. The lengths of the ECG cables 2206 can be set based on the order in which each ECG cable 2206 is to be applied to the victim. For instance, the first ECG cables 2206 to be applied, such as the six V cables, can be the shortest cables, and the last ECG cables 2206 to be applied, such as the limb cables, can be the longest cables. In some cases, the electrode pads 2212 of ECG cables 2206 of different lengths are less likely to stick together, thus improving the usability of the ECG housing 2200.

Figure 23:
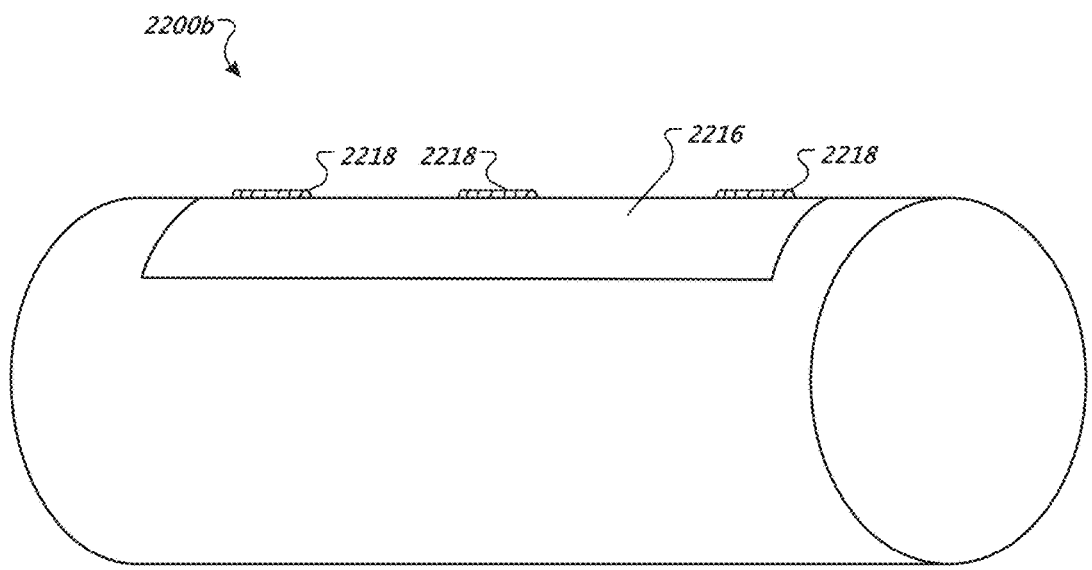

Referring to FIG. 23, in some examples, an ECG housing 2200b includes a hinged door 2216 connected to the housing 2200b by one or more hinges 2218. The door 2216 can be opened to access the pull tab. Other opening mechanisms can also be used, such as a sliding door, a clam-shell opening mechanism, or another type of opening mechanism.

In some examples, the ECG package 2200 is a single-use, disposable package. In some examples, new ECG cables 2206 can be wound around the core 2208 to reuse the ECG package.

Figure 24:
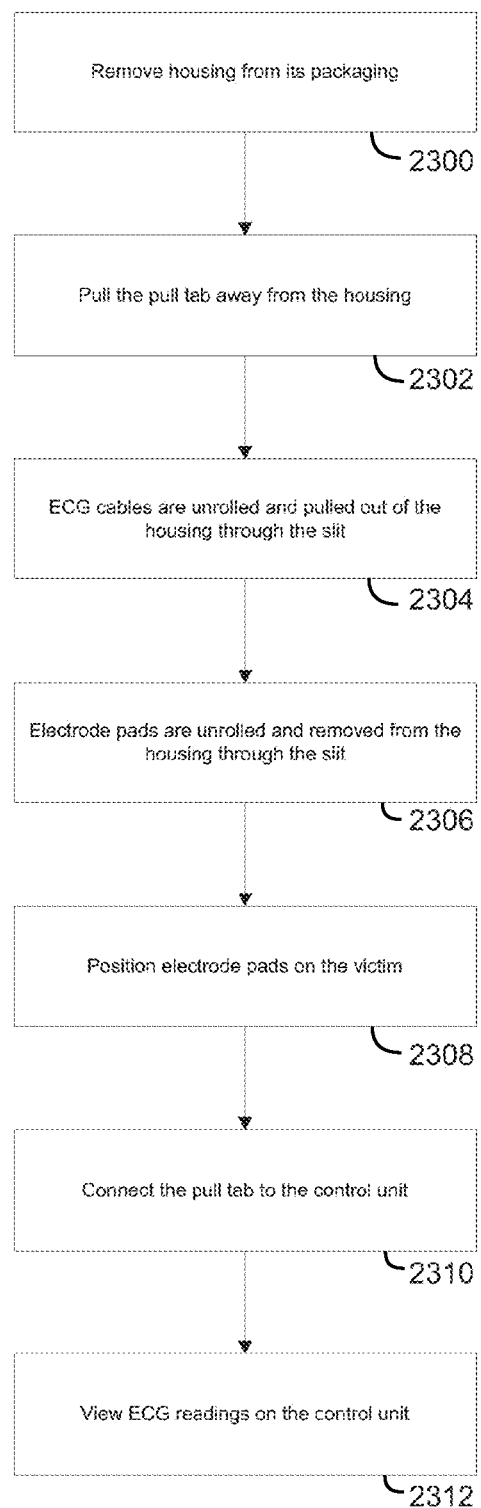
FIG. 24 is a flowchart.

Referring to FIG. 24, to deploy the ECG package 2200, the housing 2202 is removed from its packaging (2300), if present. For instance, a wrapper enclosing the housing can be cut, torn, or otherwise opened.

The pull tab 2204 is pulled (2302) away from the housing 2202, causing the ECG cables 2206 connected thereto to unwind from the core 2208. That is, the ECG cables 2206 are unrolled and pulled out of the housing through the slit 2205 (2304).

The electrode pads 2212 at the proximal ends of the ECG cables 2206 are unrolled and removed from the housing 2202 through the slit 2205 (2306). The electrode pads 2212 can be positioned at appropriate positions on the victim (2308), such as on the chest, legs, and/or arms of the victim.

The pull tab 2204 can be connected to a control unit, such as a mobile phone or tablet or another type of mobile device, or to another type of ECG-capable device. Once the electrode pads 2204 are positioned and the pull tab 2204 connected to the control unit (2310), ECG readings can be viewed on a display interface of the control unit (2312).

The features described herein can be implemented in digital electronic circuitry, or in computer hardware, firmware, software, or in combinations of them. The apparatus can be implemented in a computer program product tangibly embodied in an information carrier, e.g., in a machine-readable storage device, for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube), LCD (liquid crystal display), or other type of display monitor for displaying information to the user and a keyboard and a pointing device such as a mouse or a trackball by which the user can provide input to the computer.

The features can be implemented on a mobile computing device, such as a mobile phone, a tablet, a watch, glasses, or another type of mobile computing device. The mobile computing device can have a display device such as a touch screen for displaying information to the user and receiving input from the user. The mobile computing device can receive input from the user via the touch screen, a key pad, a microphone, or another type of input device.

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include, e.g., a LAN, a WAN, and the computers and networks forming the Internet.

The computer system can include clients and servers. A client and server are generally remote from each other and typically interact through a network, such as the described one. The relationship of client and server arises by virtue of computer programs running on the respective computers and having a client-server relationship to each other.

It is to be understood that the foregoing description is intended to illustrate and not to limit the scope of the invention, which is defined by the scope of the appended claims. Other embodiments are within the scope of the following claims.

What is claimed is:

1. A computing device adapted to be worn on a wrist, the computing device comprising:
    a sensor configured to detect movement of the wrist of a rescuer wearing the computing device;
    a processor coupled to a memory, the processor and the memory configured to generate chest compression feedback during chest compressions, applied by the rescuer to the chest of a patient, based on the detected movement of the wrist of the rescuer;
    at least one input interface comprising at least one of (i) a touch screen, and (ii) a microphone, wherein the input interface is configured to receive input from the rescuer, the input from the rescuer including at least one of: a report of an emergency to emergency medical services, patient information about the patient, a request to establish wireless communication with a defibrillator, and instructions to analyze a condition of the patient;
    at least one output device configured to provide the chest compression feedback as tactile feedback; and
    wherein the tactile feedback comprises vibrations and includes a first type of tactile feedback and a second type of tactile feedback that is different from the first type of tactile feedback.

2. The computing device of claim 1, wherein the first type of tactile feedback is indicative of a depth of the chest compressions applied by the rescuer.

3. The computing device of claim 2, wherein the chest compression feedback further includes audible feedback indicative of the depth of the chest compressions or a rate of the chest compressions applied by the rescuer.

4. The computing device of claim 3, wherein the audible feedback is indicative of a proper rate of the chest compressions that should be applied by the rescuer.

5. The computing device of claim 4, wherein the audible feedback comprises a rhythmic tone to assist the rescuer in delivering the chest compressions at the proper rate.

6. The computing device of claim 1, wherein the tactile feedback provides an indication of whether the chest compressions are reaching recommended depth during the chest compressions.

7. The computing device of claim 1, wherein the sensor comprises an accelerometer.

8. The computing device of claim 1, wherein the computing device is configured to wirelessly communicate with the defibrillator.

9. The computing device of claim 3, wherein the audible feedback comprises a voice prompt.

10. The computing device of claim 7 wherein the processor and the memory are further configured to integrate measurements of the accelerometer to provide a depth of compression.

11. The computing device of claim 1 wherein the computing device comprises one or more light emitting diodes (LEDs).

12. The computing device of claim 1 wherein the touch screen is configured to provide chest compression feedback as visual feedback.

13. The computing device of claim 8, wherein the processor is configured to control operations of the defibrillator.

14. The computing device of claim 13 wherein the operations of the defibrillator comprise one or more of a shock energy, a shock duration, and a number of shocks.

15. The computing device of claim 8 wherein the processor is configured to receive status information about the patient.

16. The computing device of claim 8 wherein the processor is configured to wirelessly communicate with the defibrillator in response to a user instruction input from the touch screen of the computing device.

17. The computing device of claim 16 wherein the user instruction input comprises identification information for the defibrillator.

18. The computing device of claim 1 comprising both the touch screen and the microphone.

19. The computing device of claim 1, wherein the computing device is configured to access a communications network.

20. The computing device of claim 1, wherein the input interface is the touch screen and the processor of the computing device is configured to prompt the rescuer to provide input by tapping a button on the touch screen.

21. The computing device of claim 20, wherein the prompt comprises an instruction to provide input related to an operational mode.

22. The computing device of claim 21, wherein the input comprises at least one of (i) selecting between a rescue mode and training mode, and (ii) selecting a level of operation.

23. The computing device of claim 1, wherein the input interface is the microphone and the processor of the computing device is configured to use speech recognition technology to recognize voice commands.

24. A computing device adapted to be worn on a wrist, the computing device comprising:
a sensor configured to detect movement of the wrist of a rescuer wearing the computing device;
a processor coupled to a memory, the processor and the memory configured to generate chest compression feedback during chest compressions, applied by the rescuer to the chest of a patient, based on the detected movement of the wrist of the rescuer;
at least one input interface comprising a touch screen that is configured to receive input from the rescuer, wherein the processor is configured to prompt the rescuer to provide the input by tapping a button on the touch screen and wherein the input from the rescuer includes at least one of: a report of an emergency to emergency medical services, patient information about the patient, a request to establish wireless communication with a defibrillator, and instructions to analyze a condition of the patient;
at least one output device configured to provide the chest compression feedback as tactile feedback; and
wherein the tactile feedback comprises vibrations and includes a first type of tactile feedback and a second type of tactile feedback that is different from the first type of tactile feedback.

25. The computing device of claim 24, wherein the first type of tactile feedback is indicative of a depth of the chest compressions applied by the rescuer.

26. The computing device of claim 25, wherein the chest compression feedback further includes audible feedback indicative of the depth or a rate of the chest compressions applied by the rescuer.

27. The computing device of claim 26, wherein the audible feedback is indicative of a proper rate of the chest compressions that should be applied by the rescuer.

28. The computing device of claim 27, wherein the audible feedback comprises a rhythmic tone to assist the rescuer in delivering the chest compressions at the proper rate.

29. The computing device of claim 24, wherein the tactile feedback provides an indication of whether the chest compressions are reaching recommended depth during the chest compressions.

30. The computing device of claim 24, wherein the sensor comprises an accelerometer.

31. The computing device of claim 24, wherein the computing device is configured to wirelessly communicate with the defibrillator.

32. The computing device of claim 26, wherein the audible feedback comprises a voice prompt.

33. The computing device of claim 30 wherein the processor and the memory are further configured to integrate measurements of the accelerometer to provide a depth of compression.

34. The computing device of claim 24 wherein the computing device comprises one or more light emitting diodes (LEDs).

35. The computing device of claim 24 wherein the touch screen is configured to provide chest compression feedback as visual feedback.

36. The computing device of claim 31, wherein the processor is configured to control operations of the defibrillator.

37. The computing device of claim 36 wherein the operations of the defibrillator comprise one or more of a shock energy, a shock duration, and a number of shocks.

38. The computing device of claim 31 wherein the processor is configured to receive status information about the patient.

39. The computing device of claim 31 wherein the processor is configured to wirelessly communicate with the defibrillator in response to a user instruction input from the touch screen of the computing device.

40. The computing device of claim 39 wherein the user instruction input comprises identification information for the defibrillator.

41. The computing device of claim 24 wherein the input interface further includes a microphone for recording a voice of the rescuer.

42. The computing device of claim 41, wherein the microphone and the processor of the computing device is configured to use speech recognition technology to recognize voice commands.

43. The computing device of claim 24, wherein the computing device is configured to access a communications network.

44. The computing device of claim 24, wherein the prompt comprises an instruction to provide input related to an operational mode.

45. The computing device of claim 44, wherein the input comprises at least one of (i) selecting between a rescue mode and training mode, and (ii) selecting a level of operation.

* * * * *